US008385604B2

(12) United States Patent
Orpen

(10) Patent No.: US 8,385,604 B2
(45) Date of Patent: Feb. 26, 2013

(54) ROCK CORE LOGGING

(75) Inventor: John Lisle Orpen, Johannesburg (ZA)

(73) Assignee: Ground Modelling Technologies, Ltd. (GB)

( * ) Notice: Subject to any disclaimer, the term of this patent is extended or adjusted under 35 U.S.C. 154(b) by 1060 days.

(21) Appl. No.: 12/281,872

(22) PCT Filed: Mar. 7, 2007

(86) PCT No.: PCT/IB2007/050764
§ 371 (c)(1),
(2), (4) Date: Sep. 5, 2008

(87) PCT Pub. No.: WO2007/102129
PCT Pub. Date: Sep. 13, 2007

(65) Prior Publication Data
US 2009/0080705 A1   Mar. 26, 2009

(30) Foreign Application Priority Data

Mar. 7, 2006 (ZA) .................................. 2006-01836
Sep. 18, 2006 (ZA) .................................. 2006-08007

(51) Int. Cl.
*G06K 9/00* (2006.01)
(52) U.S. Cl. ............................................ 382/109; 702/6
(58) Field of Classification Search .................. None
See application file for complete search history.

(56) References Cited

U.S. PATENT DOCUMENTS

| 4,759,214 | A | | 7/1988 | Sekine et al. | |
|---|---|---|---|---|---|
| 5,809,163 | A | * | 9/1998 | Delhomme et al. | 382/109 |
| 6,816,787 | B2 | * | 11/2004 | Ramamoorthy et al. | 702/7 |
| 2007/0061079 | A1 | * | 3/2007 | Hu | 702/6 |

OTHER PUBLICATIONS

R. Schepers, G. Rafat, C. Gelbke, and B. Lehman, "Application of Borehole Logging, Core Imaging and Tomography to Geotechnical Exploration", 2001, Pergamon, International Journal of Rock Mechanics & Mining Sciences, vol. 38, pp. 867-876.*
International Search Report of International Application No. PCT/IB2007/050764 dated Sep. 8, 2008.

(Continued)

*Primary Examiner* — Andrew W Johns
*Assistant Examiner* — Siamak Harandi
(74) *Attorney, Agent, or Firm* — Nixon Peabody LLP; Jeffrey L. Costellia

(57) ABSTRACT

The invention is provides a method of logging rock core. A digital photograph of core from a borehole is taken and the image is first processed. This involves calibration and correction, or un-distortion, of the digital image. A reference frame is included in the photograph to facilitate processing. The two-dimensional image is then used as a virtual three-dimensional model of the core enabling length and angle measurements to be logged. These include linear rock interval measurements as well as angular measurements of geological structures. The method is implemented using a software program which enables suitable hardware. The software program will be provided on a suitable computer readable medium. Manually logged data of the same kind is imported for comparison to data logged using the software program. All of this data can be displayed on the image and incrementally on a Stereonet as it is logged. A permanent visual record and reliable means of rapidly assessing the accuracy and quality of the data is provided. The invention also provides for automation of a significant part of the image processing and logging. The reference frame is preferably provided by a rock core tray frame having suitable indicators with known dimensions. The frame is rectangular with orthogonal lines on an upper surface. The mid-points of these lines are marked and spaced apart brackets provide for elevated lines superimposed on the orthogonal lines.

28 Claims, 21 Drawing Sheets

OTHER PUBLICATIONS

Written Opinion of the International Searching Authority of International Application No. PCT/IB2007/050764 dated Sep. 8, 2008.
Renate Sliwa et al., "ACARP Project C15037: Tool for Rapid and Consistent Capture of Drill Core Observations", Aug. 10, 2007, pp. 1-24., Report No: 2007/446, Australian Science, Australia.
Matthew Brace et al., "Investing in Interoperability", Earthmatters, Nov./Dec. 2007, pp. 1-20., Issue 15, CSIRO Exploration and Mining Magazine.
Internet Archive, Geotek Materials cited by Australian Patent Office, Feb. 2005, 12 pages.

* cited by examiner

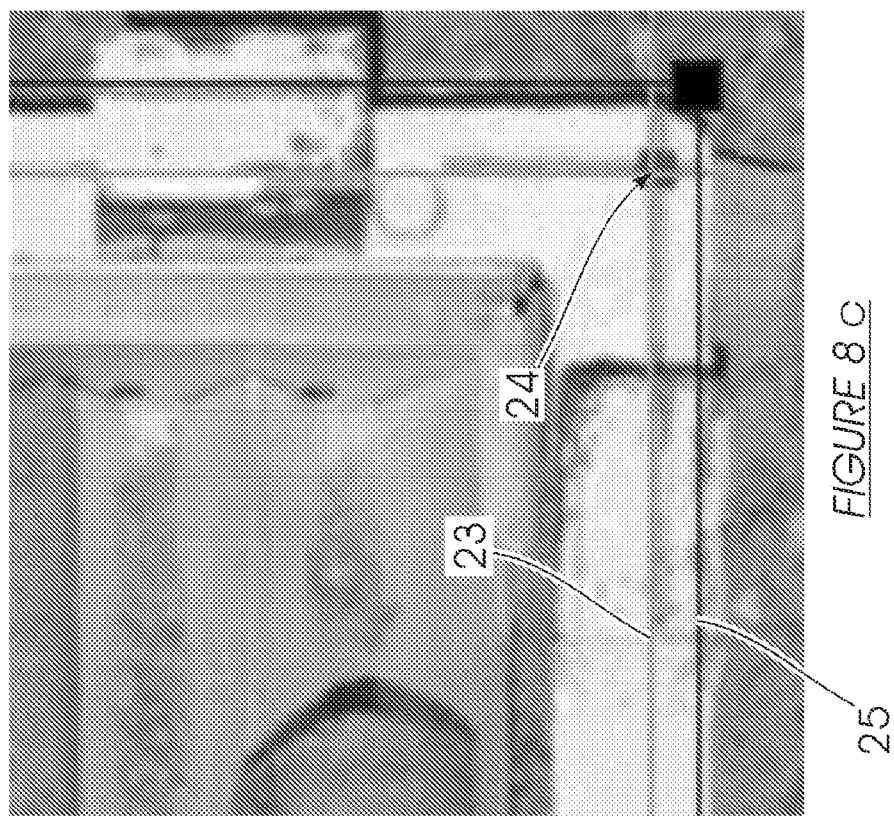

Borehole Number: GDH059

| Run No | Rods | Core Barrel Outer Tube | Core Barrel Inner Tube | TOTAL (m) | Stick Up | DEPTH of Hole | Advance | Core Rec. | Core Loss | Ground Core |
|---|---|---|---|---|---|---|---|---|---|---|
| 1 | 1 | 0.70 |  | 3.70 | 0.00 | 3.70 | 3.70 | 0.00 | 3.70 | 0.00 |
| 2 | 2 | 4.14 | 3.10 | 10.14 | 3.40 | 6.74 | 3.04 | 0.71 | 2.33 | 0.00 |
| 3 | 3 | 4.14 | 3.10 | 13.14 | 3.40 | 9.74 | 3.00 | 3.00 | 0.00 | 0.00 |
| 4 | 4 | 4.14 | 3.10 | 16.14 | 3.40 | 12.74 | 3.00 | 3.00 | 0.00 | 0.00 |
| 5 | 5 | 4.14 | 3.10 | 19.14 | 3.40 | 15.74 | 3.00 | 3.10 | -0.10 | 0.00 |
| 6 | 6 | 4.14 | 3.10 | 22.14 | 3.10 | 19.04 | 3.30 | 2.82 | 0.48 | 0.00 |
| 7 | 7 | 4.14 | 3.10 | 25.14 | 4.80 | 20.34 | 1.30 | 1.38 | -0.08 | 0.00 |
| 8 | 7 | 4.14 | 3.10 | 25.14 | 3.40 | 21.74 | 1.40 | 3.35 | -1.95 | 0.25 |
| 9 | 8 | 4.14 | 3.10 | 28.14 | 3.95 | 24.19 | 2.45 | 2.45 | 0.00 | 0.00 |

Table 1.

Borehole No:                 Core Orientation Log

| Run No | From | To | Core Rec. | Orientation Mark Y/N? | If Yes - offset from previous (degrees +/-) | If No - Forward or Back marked? | Length Marked | Length Unmarked | Comment |
|---|---|---|---|---|---|---|---|---|---|
|  |  |  |  |  |  |  |  |  |  |
|  |  |  |  |  |  |  |  |  |  |
|  |  |  |  |  |  |  |  |  |  |

Table 2.

Borehole Survey Log

Borehole No:

| Depth (m) | Inclination | Bearing |
|---|---|---|
| 0 | -49.25 | 162.00 |
| 3 | -49.36 | 162.00 |
| 6 | -51.24 | 162.35 |
| 9 | -49.33 | 162.70 |
| 12 | -49.34 | 163.05 |
| 15 | -49.3 | 163.40 |
| 18 | -49.28 | 163.75 |
| 21 | -49.34 | 164.10 |
| 24 | -49.36 | 164.45 |
| 27 | -49.34 | 164.80 |
| 30 | -49.34 | 165.15 |

Table 3.

*FIGURE 19*

ROCK CORE LOGGING

FIELD OF THE INVENTION

The invention relates to a method for logging data from drilled core samples of rock. The invention extends to a software program, and to a computer readable medium and a combination of hardware.

BACKGROUND TO THE INVENTION

The successful exploration for, delineation of, and eventual mining of ore-bodies, as well as the safe construction of massive structures such as high rise buildings and dam walls, and tunneling for civil works etc. are all dependent on a thorough knowledge of the geology of the ground. A three-dimensional (3D) understanding of the subsurface is developed from surface geological mapping, along with geophysical and geochemical surveys. However, the predictive power of such three-dimensional models is substantially limited without data from reliable and accurate measurements derived directly from the subsurface.

Various drilling techniques (such as diamond drilling) are used to bore deep into the earth with the aim of producing continuous cylinders of rock, termed "core", which samples are then measured and described in a process known as "core logging". These data are then processed and analyzed to refine the three-dimensional modeling as well as determine such parameters as ore body size and grade, or the potential for other "hidden" ore deposits/extensions, as well as blasting requirements, rippability of the rock and rock mass behavior characteristics (such as slope stability, fragmentation, flow or creep etc.) when excavating or loading with additional weight and so on.

Core logging entails the measurement and detailed description of a wide range of features—the lengths of lithological and alteration intervals for example, the densities of the different rock types intersected, their uniaxial compressive and tensile strengths, the shear strengths of any contained discontinuities, as well as the attitude of all structures, both planar (bedding, fractures, joints etc.) and linear (fault slickensides, acicular mineral alignment etc.) relative to the core axis. Additional tasks include evaluating the length of missing sections of core due either to natural cavities or mechanical grinding and poor drilling practice and defining the lengths of solid core versus rubble or matrix, or badly fractured and/or friable rock.

Current core logging methods do not achieve optimum results. They are largely manual in that data is handwritten on either standard or customized logging forms. These data are then clerically entered into a computer data base and returned to the geologist for editing, validation and processing. This time consuming process is fraught with transcription, editing and audit errors, to the detriment of both the drilling program and the ground interpretation/modeling exercise.

Three-dimensional ground modeling is further severely hampered by the fact that the collection of subsurface structural data is still erroneously considered too specialized and expensive to run routinely. In reality only two procedures to prepare the core for such measurements are needed. Firstly, the intersection of the in-situ geographic vertical plane with the rock core has to be marked along the surface of the cylinder. Several different instruments can be used to indicate the position of such a reference line, which when drawn on the core is known as an "orientation line". Then the attitude, or inclination, of the core axis has to be surveyed along the entire length of the bore, which data together with measurements of the down-hole change in core axis direction, or azimuth, is known as a "borehole survey". Given this information the angular attitude of planar or linear structures found in the core can be measured relative to the core axis and orientation line, and the results computed to derive the actual in-situ dip and dip direction, or plunge and trend of the planar and linear geological structures respectively.

The borehole survey is also required in order to calculate the geographic coordinates of features logged in the core, before the data can be processed to construct a meaningful three-dimensional model. Such modeling then requires statistically valid data to develop a reliable schematic of the ground. One of the main tools for statistically analyzing three-dimensional geological data is the stereographic projection, or Stereonet, on which the geologist should plot each and every structural data reading. The resulting Stereoplot is then contoured from which statistically valid mean values are derived for the various planar and linear structures logged in the core.

This systematic processing approach enables filters to be applied to the data at any stage of the logging process not only to evaluate accuracy, but also to display how the structures (faults, joints, shears etc.) change with depth in the ground as well as how they are influenced by the different lithologies, rock properties etc.

OBJECT OF THE INVENTION

It is an object of the present invention to provide a method of rock core logging and associated software program which facilitate the direct, digital recording of details of a core sample, together with data processing and analysis. A core tray frame and core tray suited to this are also provided.

SUMMARY OF THE INVENTION

In accordance with this invention there is provided a method of logging rock core, which includes taking a digital photograph of core from a borehole and recording structural measurements of features of the core from the photograph using a computer.

The invention further provides for the photograph to be taken of a series of rock core runs; for a longitudinal reference line to be drawn along the core; and for the line to be an orientation line (marking the intersection of the in situ geographic vertical plane with the surface of the rock core).

Further features of the invention provide for the structural measurements to include linear rock interval measurements and/or angular measurements of geological structures (structural planes or lineations); for the linear measurements to include the depth of each core run and the depth of each geological structure; and for the angular measurements to include α angle, β angle and/or θ angle of geological structures.

Further features of the invention provide for the photograph to be calibrated to a measurement scale; for the measurement scale to be photographed with the core; for the photograph to be corrected for radial distortion, pitch distortion and/or yaw distortion; for the photograph to be corrected for depth perspective (the vanishing point of the image); for a correction scale to be included in the photograph to make corrections for radial distortion, pitch distortion, yaw distortion and/or depth perspective; and for the photograph to be marked for corrections relating to at least depth perspective. Such un-distortion and correction allows the two-dimensional image to be used as a virtual three-dimensional model of the core enabling accurate length and angle measurements to be made from the image.

Further features of the invention provide for a reference frame to be used to provide a measurement and correction scale; and for the frame to extend along the length and width of a core tray. The scale is preferably provided by a rock core tray frame which includes an upper surface having indicators with known dimensions.

A further feature of the invention provides for the core to be photographed with core blocks indicating depth between each run. These depths will be provided as readings taken by the driller.

A further feature of the invention provides for the manually logged data to be collected and compared to the structural measurements from the photograph.

In accordance with another aspect of this invention there is provided a software program enabled to receive a digital image of rock core from a borehole and to make structural measurements of features of the core from the image.

The invention further provides for the software program to calibrate the image to a measurement scale; for the software program to be enabled to register indicators on a correction scale and to correct the image for depth perspective, radial distortion, pitch distortion and/or yaw distortion; for the software program to automatically calibrate the image to a measurement scale and/or correct the image to a correction scale for depth perspective, radial distortion, pitch distortion and/or yaw distortion; and for the software program to mark the image for corrections relating to at least depth perspective.

A further feature of the invention provides for the image to be taken of series of rock core runs and a measurement and/or correction scale.

Further features of the invention provide for the structural measurements to include linear rock interval measurements and/or angular measurements of the geological structures; for the structural measurements to include the depth of each core run; and the depth, $\alpha$ angle, $\beta$ angle and/or $\theta$ angle of a geological structure (structural plane or lineation).

Further features of the invention provide for the software program to enable marking of the image over geological structures and/or the ends of core segments; for the length of each segment of core and the depth of each geological structure in the image to be measured; and for the software program to provide a depth registration of the total core length (from collar to end-of-hole); and for the software program to incorporate in the depth registration details of core loss/gain along the length of the bore.

A further feature of the invention provides for the angular and/or linear measurement results to be permanently stored on the image in the form of markings, at the ends of core segments and structures measured in the core, and coded tags, on each segment for interval (lithological, physical characteristics) data. The markings are preferably coloured traces overlying the ends of core segments and structures measured in the core.

A further feature of the invention provides for the software program to be enabled to import manually logged angular (structural) and/or linear interval (lithological) data for comparison to data logged by the software program; and for the software program to display the imported data on the image. In the case of structures the results are displayed as digital coloured traces overlying the planes in the core and in the case of interval data each core segment is flagged with a coded tag. This aspect allows for full visual validation of the data and for immediate correction of any discrepancies (the invention thus provides for the importation and auditing of manually logged data).

The invention extends to a computer readable medium carrying the software program as defined above and a combination of hardware enabled by the software program defined above.

In accordance with another aspect of this invention there is provided a method of logging rock core comprising, taking a digital photograph of rock core, sending the photograph to an image processing computer where the image is:
calibrated to a measurement scale;
corrected for radial distortion, pitch distortion and/or yaw distortion; and
corrected for depth perspective
and returning the image from the processing computer for recording structural measurements of features of the core using a logging computer.

The invention further provides for the photograph to be marked by the processing computer for corrections relating to at least depth perspective. Further features of the invention provide for the image to be marked with indicators on a reference frame and/or on the core and for the processing computer to recognize the indicators and to automatically:
calibrate the image;
correct the image for radial distortion, pitch distortion and/or yaw distortion;
mark the image for corrections relating to at least depth perspective; and
depth register the core.

The length of each segment of core in the image is digitised and measured, and a depth registration of total core length (from collar to end-of-hole), incorporating details of zones of core loss/gain along the length of the bore is provided.

Further features of the invention provide for the image to be transmitted to and from the processing centre via a communication network; and for the network to include the Internet.

In accordance with another aspect of this invention there is provided an image processing software program that will receive a digital image of a series of rock core runs from a borehole and enabled to:
calibrate the image to a measurement scale;
correct the image for radial distortion, pitch distortion and/or yaw distortion; and
correct the image for depth perspective.

A further feature of the invention provides for the processing software program to store data relating to indicators on a reference frame and to automatically calibrate and correct the image from the stored data; and for the software program to enable marking of the image with traces over the geological structures and/or the ends of core segments.

In accordance with another aspect of this invention there is provided a rock core logging software program that will receive a digital image processed by the processing software program defined above and enabled to make linear and/or angular measurements of the core features from the image.

A further feature of the invention provides for the logging software to recognize traces and/or markings in the processed image and to automatically calculate at least some of the measurements. (This avoids the step of adding relevant markings as part of the logging procedure.)

Further features of the invention provide for at least some of the markings to be provided on the core prior to photography and/or by indicators provided on a core tray or a reference frame and/or by depth markers provided by core blocks.

Markers on the core can be made manually and will include an orientation line and traces or markings traced over structures on a core sample.

In accordance with another aspect of this invention there is provided a rock core tray frame having indicators with known dimensions.

The invention further provides for the indicators to provide a calibration scale and a correction scale.

Further features of the invention provide for the frame to be rectangular with indicators on an upper surface marking intersections of length and breadth adjacent corners of the frame.

Further features of the invention provide for orthogonal lines to provide the indicators on the surface between the intersections of length and breadth; for the indicators to include lines extending across elevated portions parallel to the upper surface of the frame; and for the portions to be steps on the upper surface providing elevated surfaces.

Further features of the invention provided for the midpoints of the length and breadth to be marked with indicators; and for the elevated portions to be provided to either side of the mid-points.

Further features of the invention provide for the frame to have adjustable supports; for the support to be extensible legs; and for the legs to have a screw threaded connection to the frame. This provides for the upper surface to be lined up with the top sides of core samples in a core tray.

Further features of the invention provide for the indicators on the frame to be suited for recognition in a digital image by a software program; and for the frame to be white and/or the indicators primary colours.

BRIEF DESCRIPTION OF THE DRAWINGS

These and other features of the invention will now be described, by way of example only, with reference to the accompanying drawings, in which

FIG. 8a shows a calibrated and corrected version of the image in FIG. 7;

FIG. 8b shows a magnified portion of the image in FIG. 8a;

FIG. 8c shows a further magnified portion of the image in FIG. 8a;

FIG. 9b shows a magnified portion of a processed image like that in FIG. 9a;

FIG. 9c shows the image of FIG. 9b with a trace being edited;

FIG. 11a shows a schematic illustration for the calculation of α and β angles for a planar feature using a software program;

FIG. 11b shows a portion of an image as represented by FIG. 10a;

FIG. 19 shows three tables for use in recording borehole details.

DETAILED DESCRIPTION OF THE INVENTION

Figure 1:
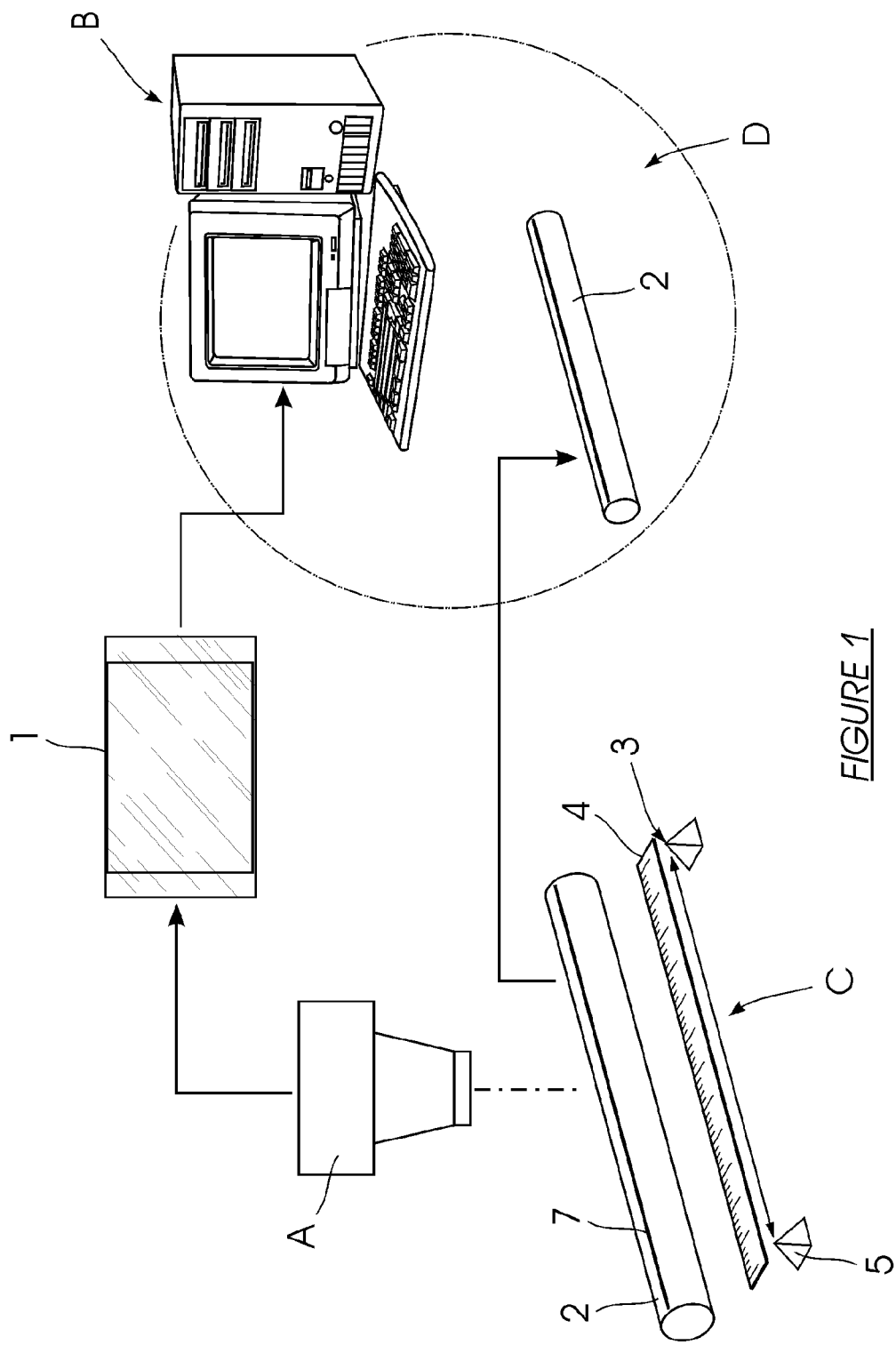
FIG. 1 shows a schematic illustration of a method of logging rock core.

Referring to FIG. 1, the current invention involves using a digital photograph (1) of rock core (2) from a borehole for logging of structural data. The image (1) is taken using a suitable digital camera (A) and downloaded to a data processor or computer (B) for analysis using a software program which is also part of this invention. Incorporated in the image (1) is a suitable measurement and calibration scale (C) which is located next to the core (2). The measurement scale is a ruler (4), in either metric or imperial measure, for calibrating pixel size to standard measure. Shown more clearly in FIG. 2, the reference scale is represented by three pyramids (5) of known dimension and spacing. The pyramids (5) are located symmetrically at three corners of a core tray (6), with a pair of rulers (4) extending therebetween. The points (3) of the pyramids (5) are lined up with outer edges of the rulers (4).

During a drilling operation, a driller will produce a series of core runs (2) in the usual manner. Once removed from the core-barrel, the core (2) is laid out on an angle iron (not shown) and marked with a reference line (7) along its length. If oriented, this will be the orientation line (7) which normally represents the bottom side of the core (2) in the geographical vertical plane (depending on the orientation method used).

Figure 2:
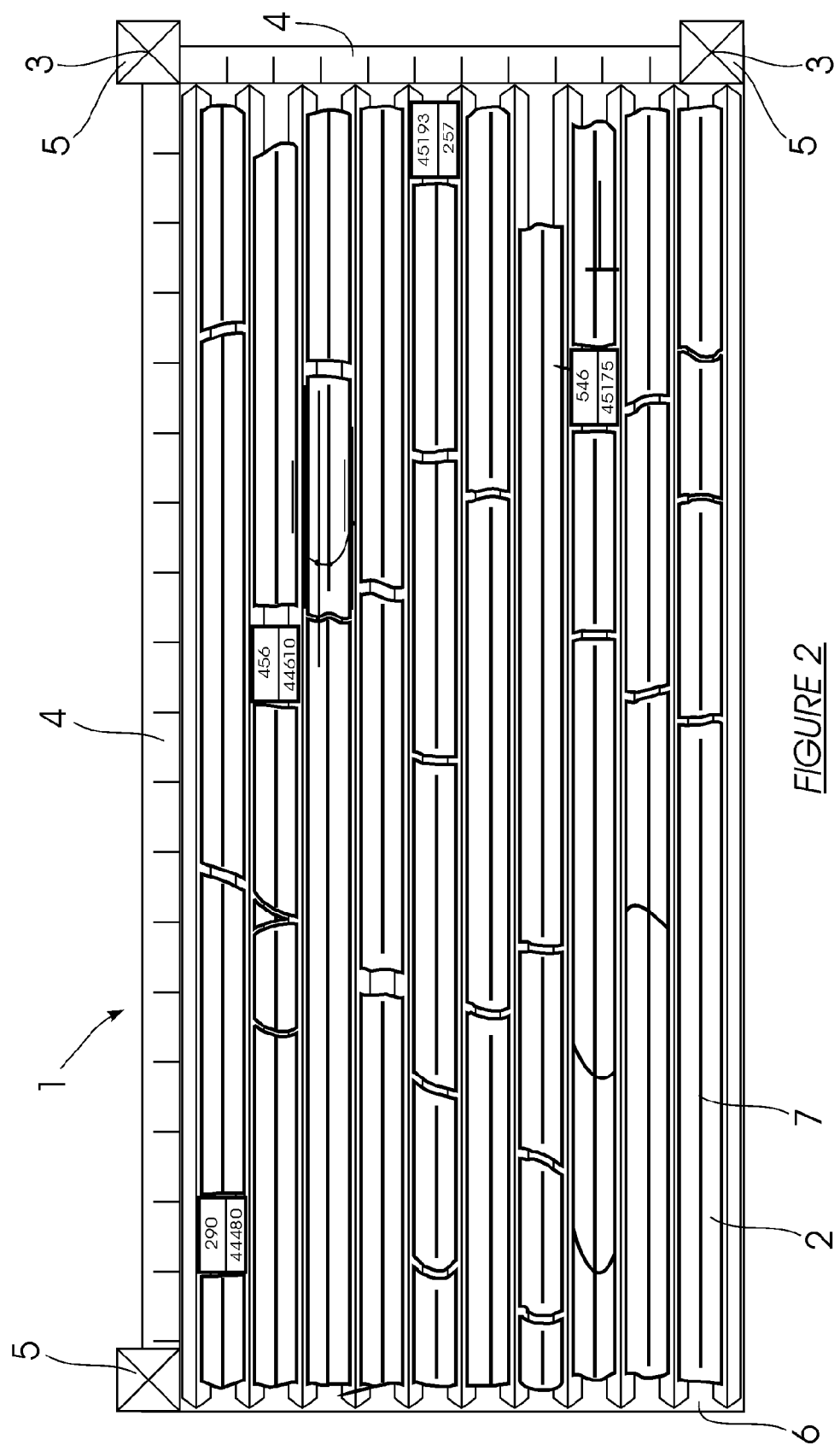
FIG. 2 shows an illustration of a photograph of a series of core runs.

Each run of core (2) can then be photographed to provide a separate image. However, a number of core runs (2) are preferably transferred to a core tray (6), with the reference line (7) visible and as close to the crests of the core segments as possible, and then photographed, as shown in FIG. 2.

Most of the data will be recorded using a cursor on the computer screen and "clicking" onto visible structure of the image (1) using a "mouse". The image (1), which is taken by the digital camera (A), will be calibrated by clicking on spaced apart points corresponding to a specific measurement. These will conveniently be the points (3) of the pyramids (5) which are located as accurately as possible in the same plane as the crests of the core (2).

The image (1) is also corrected for radial distortion, pitch distortion and yaw distortion as well as for depth perspective. This is done using the pyramids (5). The relative offset of each pyramid point (3) as seen in the image (1) from the centre of each side of the pyramid base is used for this. The distance between the points (3) and base is also known. These corrections are significant for the angular calculations which are discussed below.

The calibration and un-distortion or correction, allows the two-dimensional image (1) to be used as a virtual three-dimensional model of the core (2) enabling accurate length and angle measurements to be made from the image (1). More particularly, these are angular measurements of geological structures (structural planes or lineations) and linear rock interval measurements. The angular measurements to include calculation of the alpha ($\alpha$) angle, beta ($\beta$) angle and/or theta ($\theta$) angle of a geological structure. The linear measurements include the depth of each core run and the depth of each geological structure. The measurements referred to will be described in more detail in what follows.

The invention involves a method of logging designed to provide accurate geotechnical data that is fully auditable from oriented rock core. More particularly, digital photography of the core is processed to remove radial (lens) distortion, correct pitch and yaw perspective, and compensate for depth perspective. This is done to enable: (a) precise depth measurement, (b) accurate $\alpha$ and $\beta$ angle measurement of all planar structures in the rock as well as $\theta$ angle measurement for linear features and (c) comprehensive description of the core.

In a development of the invention, digital photographs taken of the core in a core tray with a suitable reference frame are calibrated and corrected, as described below, using a dedicated image processing software program. The processed images are then, together with the relevant driller's log, imported into a separate logging software program for recording details from the images. This is illustrated with reference to FIG. 3. The processing software is loaded onto a first computer (E) and the logging software onto a second computer (F).

It will however be appreciated that the image processing and logging software can be integrated as a single program loaded onto a single computer (B) as shown in FIG. 1.

A permanent visual record and reliable means of rapidly assessing the accuracy and quality of the data is provided in the recorded image (1). This can be seen in FIG. 9 where such an image is shown as part of a screen in the logging software program.

Details are reflected on the image (1) and also in data sets or tables of the logging software program. In addition, the data will be analyzed in conjunction with the borehole survey and plotted incrementally on a Stereonet and in any other useful manner that may be required. Different views of the image with markings and details can be selected. It can therefore be viewed with no markings or only markings and details of a specific category if that is desired.

Other recorded details, for point and interval logs as described below, can be viewed by locating a computer cursor over the relevant portion of core (or on a marker for the portion). A pop-up list or coded tags with the information will then appear on the computer screen.

Furthermore, all manual measurements taken from the core (separate from the image processing and computer logging) are imported into a data set and are also displayed in their correct depth locations on the image. This enables full auditing of all such manual logs.

Customizable pop-up window forms are used for comprehensive description of each of the fractures or structural planes so that all geotechnical detail is immediately recorded in the database.

The method of the invention may be implemented as a system divided into the following five phases:
(i) Core preparation—this requires close monitoring by the geologist involved to ensure that the driller delivers quality core from a bore that is on target;
(ii) Core photography—To be carried out as soon as possible after the core has been loaded into the core tray before it is degraded by transport and weathering, etc.;
(iii) Image processing and logging—undertaken by trained operatives using the image processing and logging software (these people are preferably chosen for their meticulous attention to detail and abilities to consistently produce accurate depth registered images with good structural detail processing);
(iv) Descriptive core logging—normally done in the core shed. Since linear and angle measurement of the core is taken care of in the image processing phase, the geologist can now concentrate on adding accurate and detailed descriptions of the various core features to the database using the logging software; and finally
(v) Data analysis phase—for this a borehole survey must be loaded onto the logging software to rotate the raw data and automatically plot the Stereonet which actively updates as each new data set is added.

Given regular single shot surveys as drilling progresses the "data analysis phase" enables a geologist to monitor the development of the Stereoplot (data plotted on the Stereonet) and investigate any unexpected data points to ensure their validity and if necessary correct any improper core orientation, for example, before it becomes a serious issue.

To begin with, the quality of any geotechnical data derived from core is greatly dependent on the quality of the drilling. The geologist involved should monitor this to minimize detrimental aspects such as: grinding or mechanical damage (apart from that necessary to break the core at the end of a drill run or to fit into the core tray); borehole deviation from target; good depth control for accurate marking of the core blocks; reliable core orientation, etc.

The current system offers on-site procedural training for the geologist as well as various aids that have been devised to ensure that core delivery is of the highest standard. This will include recording information such as that provided for in Tables 1, 2 and 3 of FIG. 19.

Once the core (2) has been recovered to surface it is assembled on a suitable length angle iron and marked up with the orientation line (7). All breaks are then marked with a proper description (such as natural, mechanical or due to grinding, washed away etc.). The recovery is measured and the core photographed before packing it into a core tray. Any subsequent unmarked breaks can thus be confidently treated as mechanical.

Figure 3:
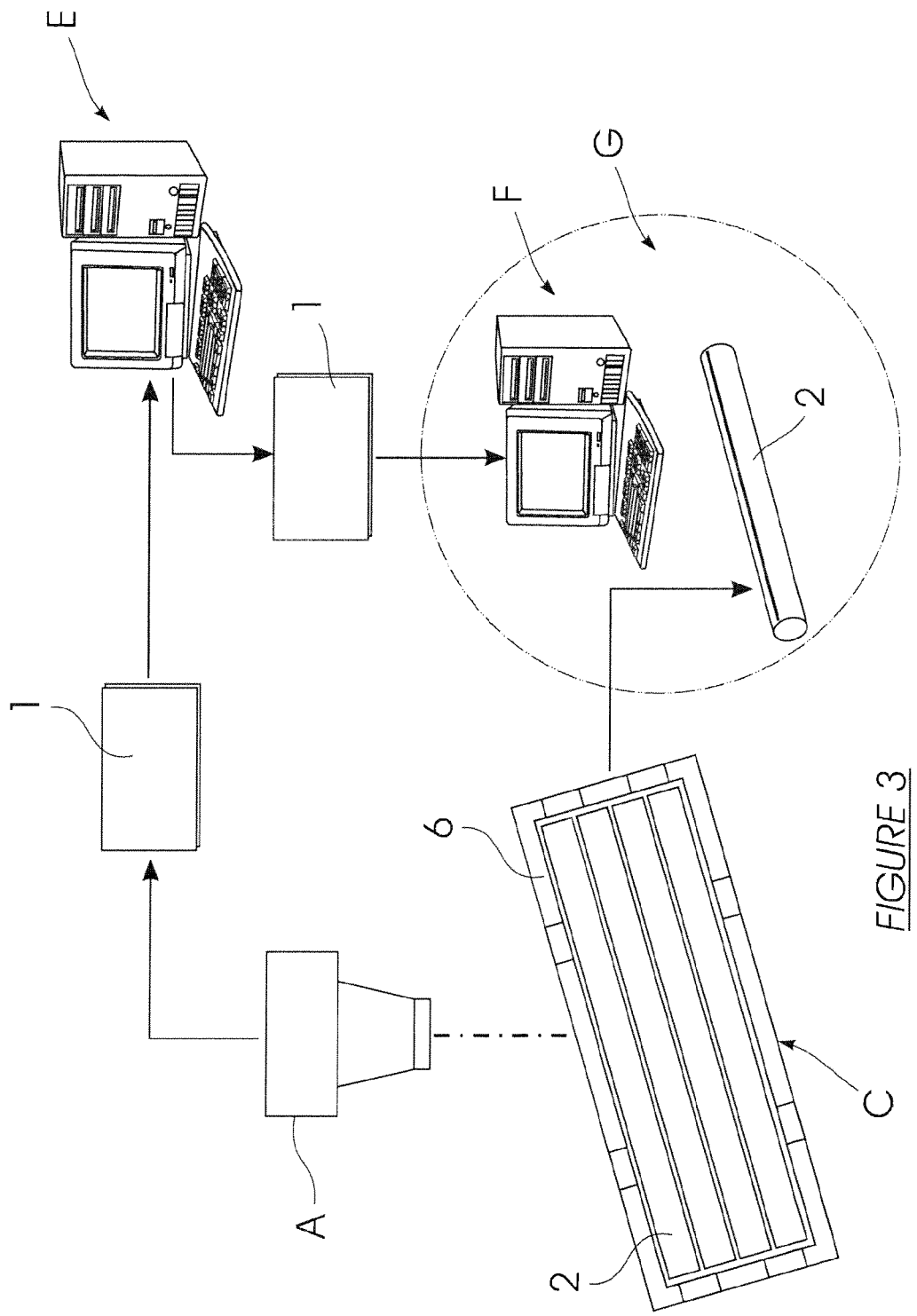
FIG. 3 shows another schematic illustration of a method in accordance with this invention.

Referring to now to FIG. 3, the core (2) is photographed in a core tray (6) on a flat concrete slab in a well lit area, but not in direct sunlight. A digital camera (A) is preferably mounted on a tripod (8) such that it is relatively horizontal and central to the tray (6).

Figure 4:
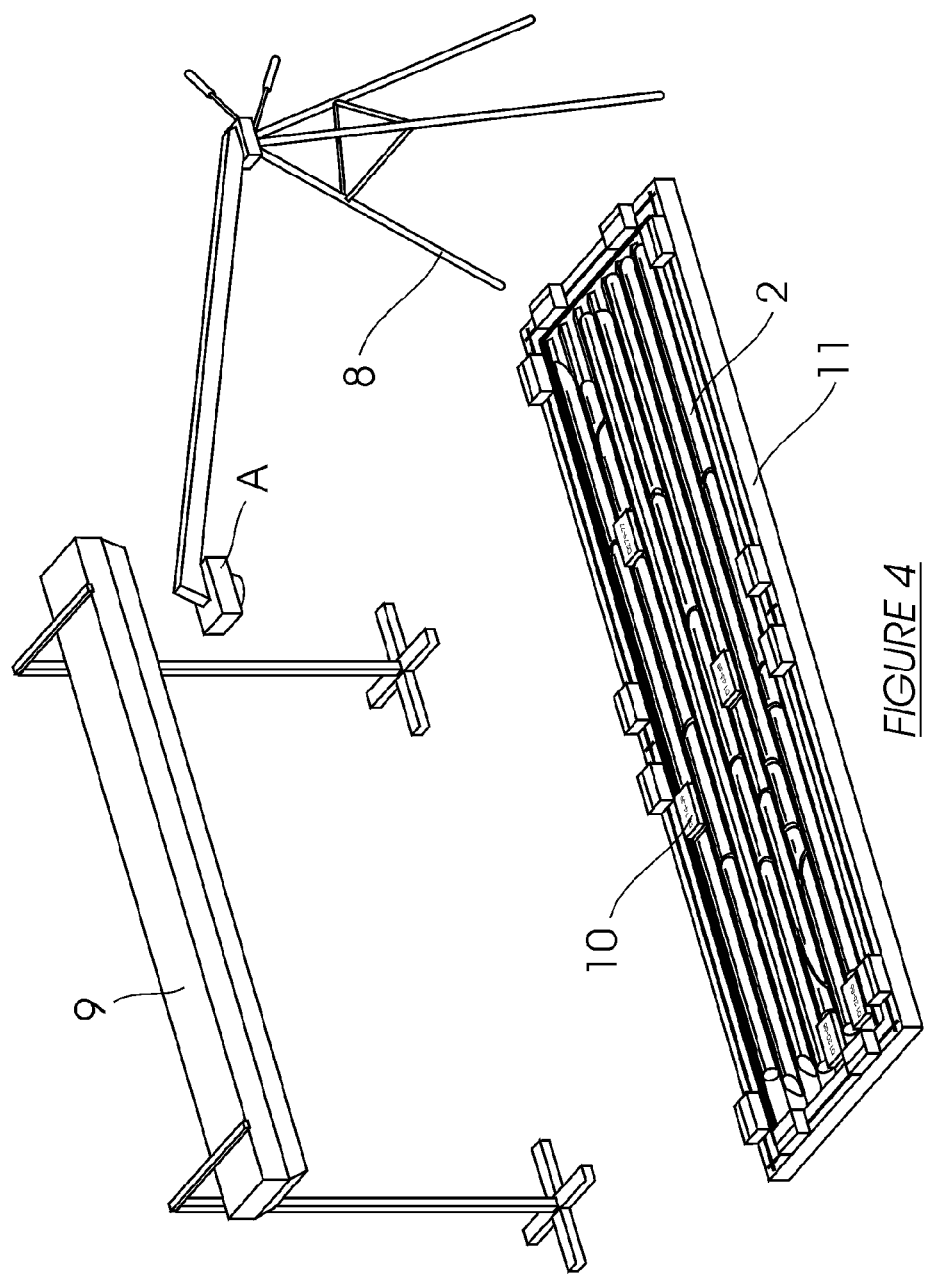
FIG. 4 shows an arrangement of equipment for photographing core samples.

FIG. 4 shows the camera tripod and lighting setup. A fluorescent light (9) is included. Core blocks (10) are turned so that the depth marked on each is clearly visible in the photograph image (1). A rigid, calibration and correction frame (11) is placed around each tray (6) for the photograph (1).

Figure 5:
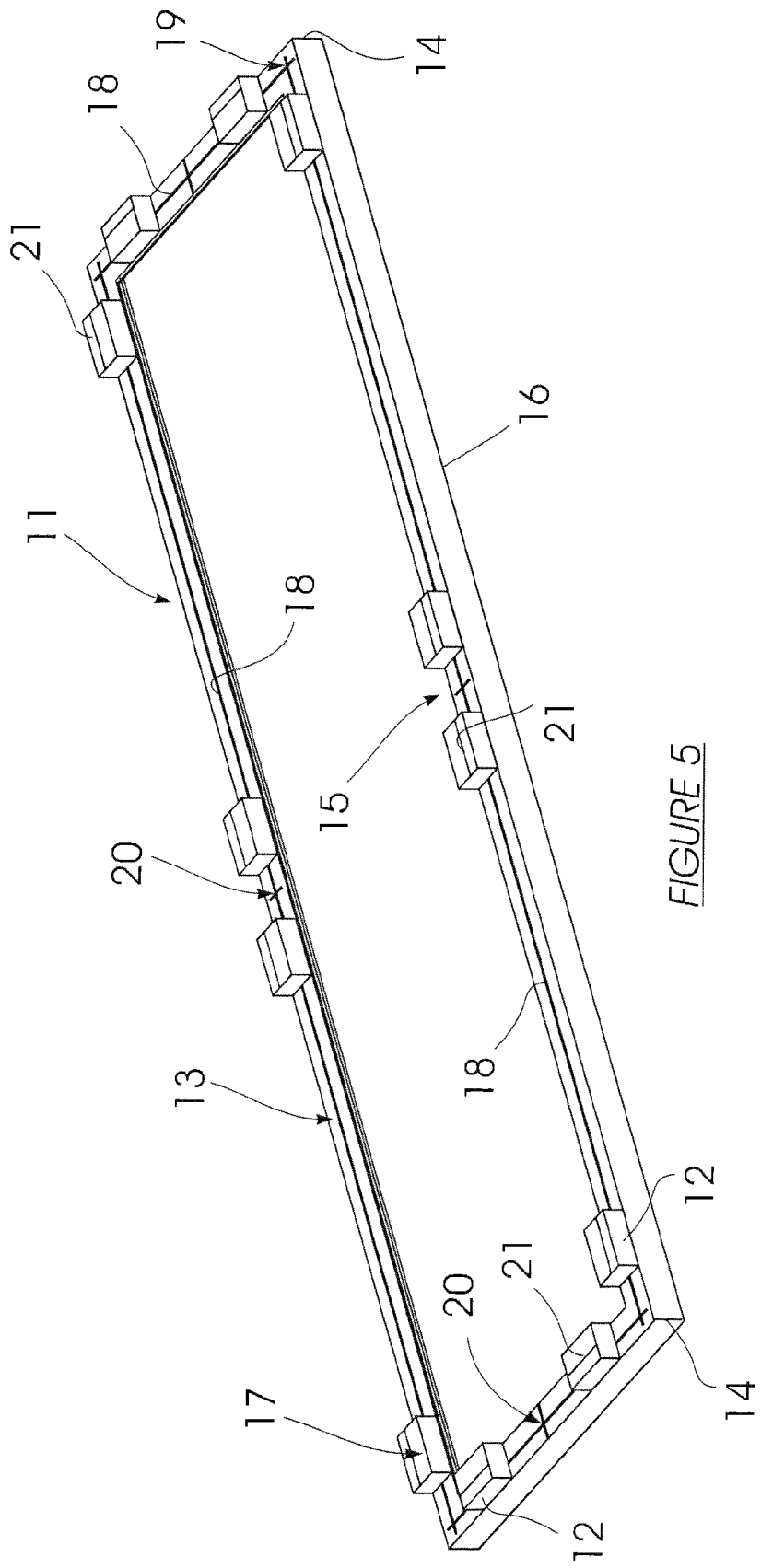
FIG. 5 shows perspective view of a core tray reference frame.
Figure 6:
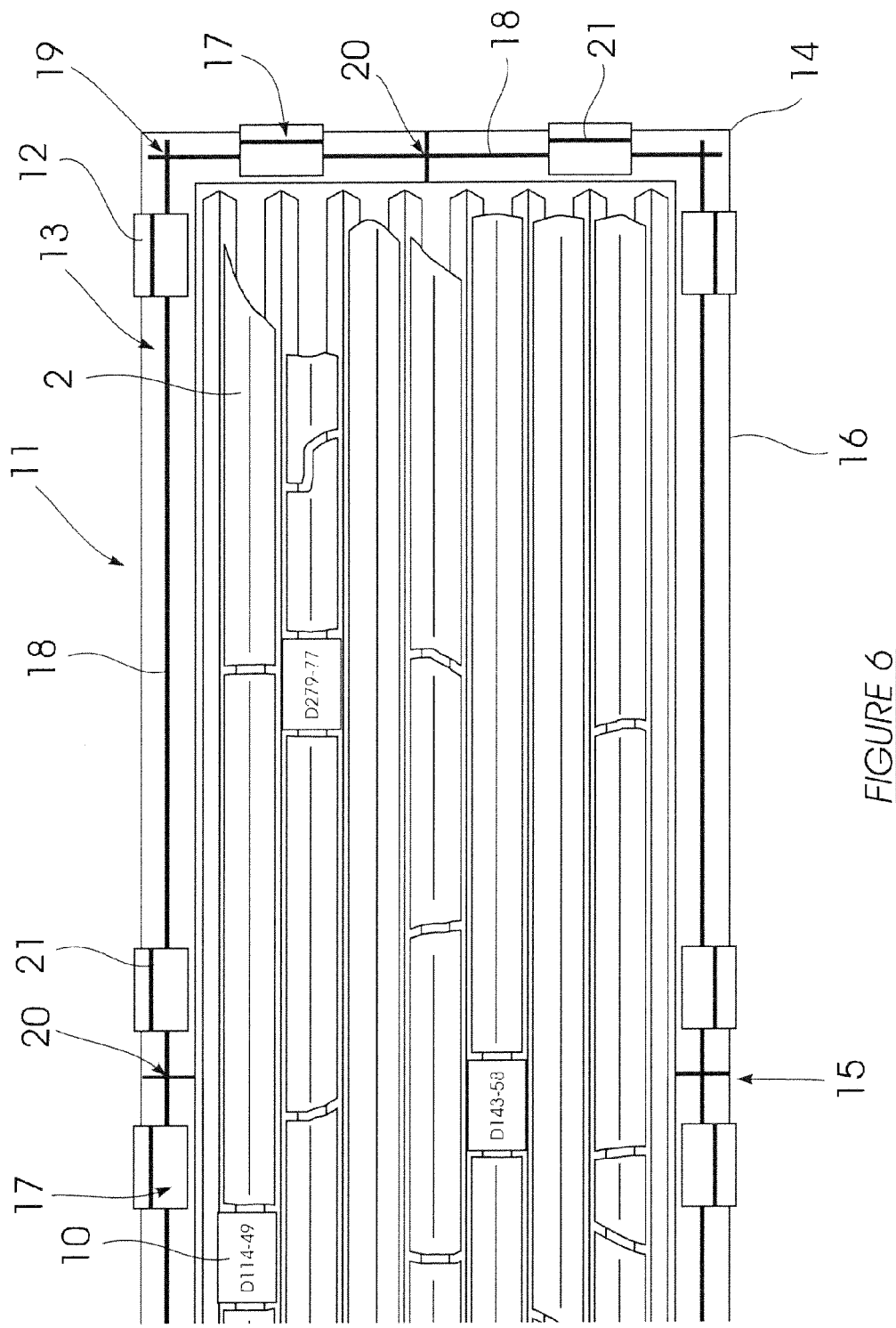
FIG. 6 shows part of a processed digital image of a core tray with core positioned within a core tray frame.

The frame (11) which is shown more clearly in FIG. 5 can be made from angle iron welded to provide the required rectangular form. Brackets (12) are attached on the upper surface (13) of the frame (11) to either side of the corners (14) and to either side of the mid-points (15) along the length, or long sides (16), of the frame (11). The brackets (12) are provided by inverted sections of channel iron. These brackets (12) provide twelve elevated surfaces (17) that are parallel to the upper surface (13) of the frame (11) on which they are mounted. The frame (11) is painted white.

The reference frame (11) is marked along the centre of the upper surface (13) with orthogonal lines (18), which cross each other at (19) adjacent the corners (14) of the rectangular frame (11). It is also marked with crosses (20) at the mid-points of each side (length and width). These indicators provide a calibration and correction scale, the significance of which will become further apparent from what follows.

The lines (18) and crosses (20) on the upper surface (13) are green. Blue lines (21) on the elevated surface (17) of each of the brackets (12) are provided vertically above the green lines (18) and (20) which extend along the frame (11) below.

Figure 7:
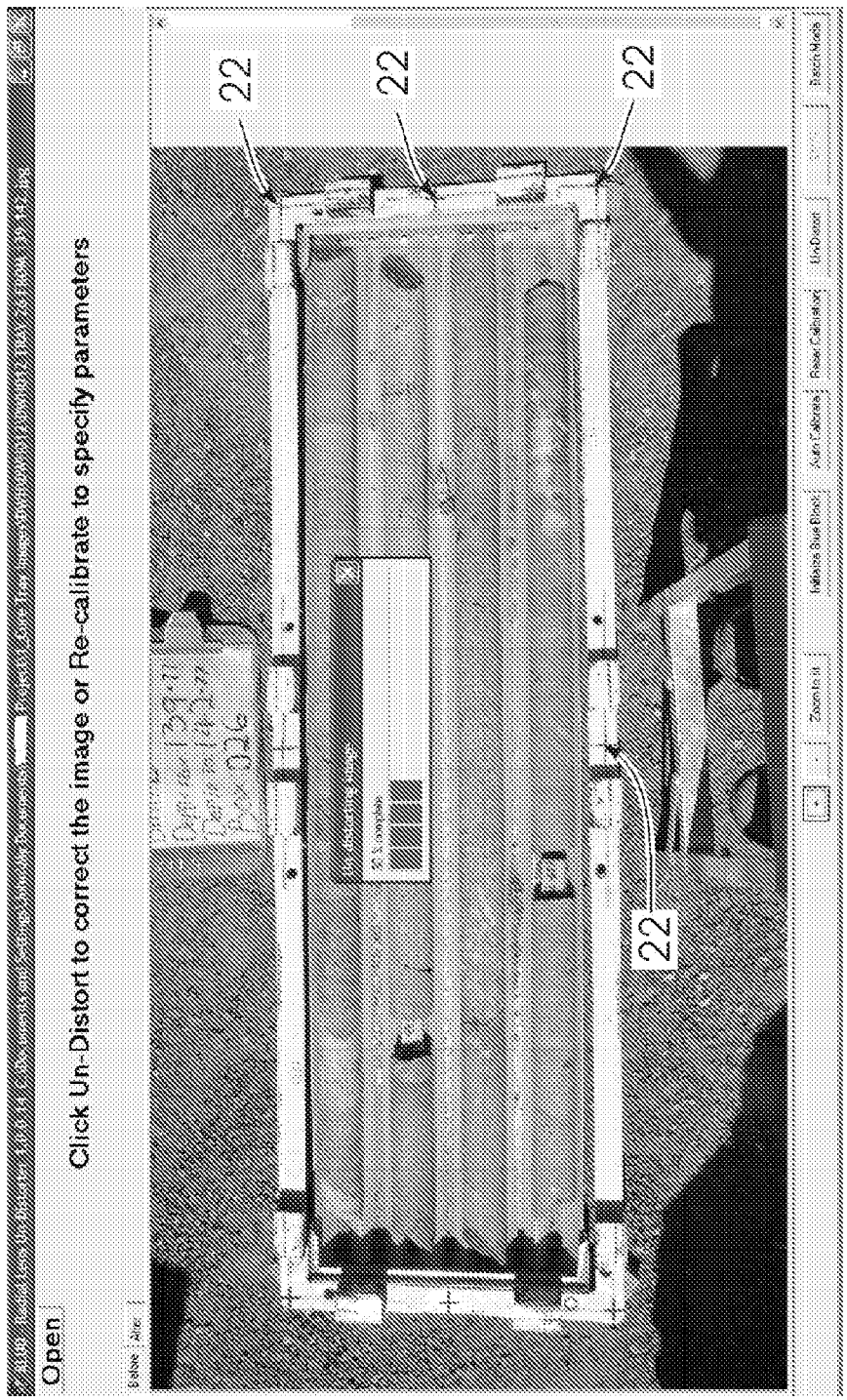
FIG. 7 shows a photograph image in the process of calibration and correction.

The digital image (1) is imported to the processing software on computer (E). The image processing program will request the length and width of the frame (11) between the crosses (19). In this example, the values are 1.623 m and 0.44 m. The diameter of the core is also provided. The image (1) is then calibrated by clicking the cursor from corner (19) to mid-point (20) to corner (19) indicator, on each of the cross markings on the frame (11) in sequence as prompted by the software program. The prompts require, in addition to each of the corners (19), for the four mid-point (20) indicators to also be clicked. When this is done, a red cross (22) is left superimposed at each of the corners (19) and mid-points (20) where the cursor has been clicked. This is shown in FIG. 7.

The relative displacements of the red crosses (22) at the corners (19) and mid-points (20) in the image (1) in relation to the actual dimensions of the known orthogonal reference frame (11) are used to remove radial distortion and correct pitch and yaw perspective in each image (1). This step is executed through the image processing software and referred to as "un-distort" in this document. To optimize this adjustment calculation, the frame (11) and core tray (6) assembly are arranged so that (i) the core (2) is turned so that the orientation line (7) is clearly visible in an upper position, as near as possible to the crest of each segment (2) and (ii) the upper surface (13) of the frame is level with the crests of the core (2).

To achieve the latter, the frame (11) must be adjustable in its height relative to the tray (6) [or the tray needs to be configured for relative adjustment]. In this embodiment the frame (11) has extensible legs providing adjustable supports (not shown). The legs can be bolts adjacent each of the corners (14) with a screw threaded connection to the frame (11). This enables the upper surface (13) to be lined up with the top sides of core samples (2) in a core tray (6).

Figure 8:
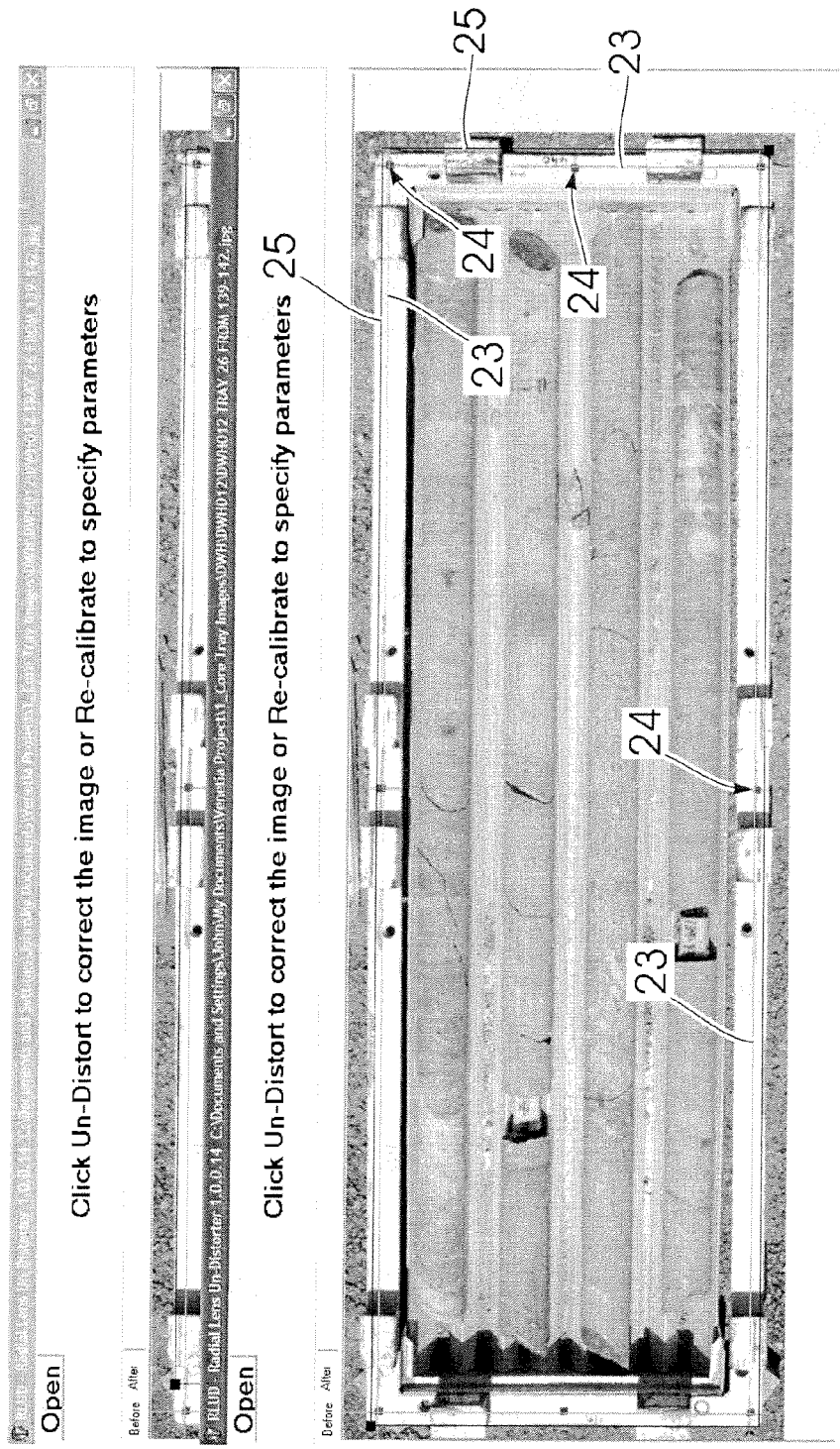
Figure 8:
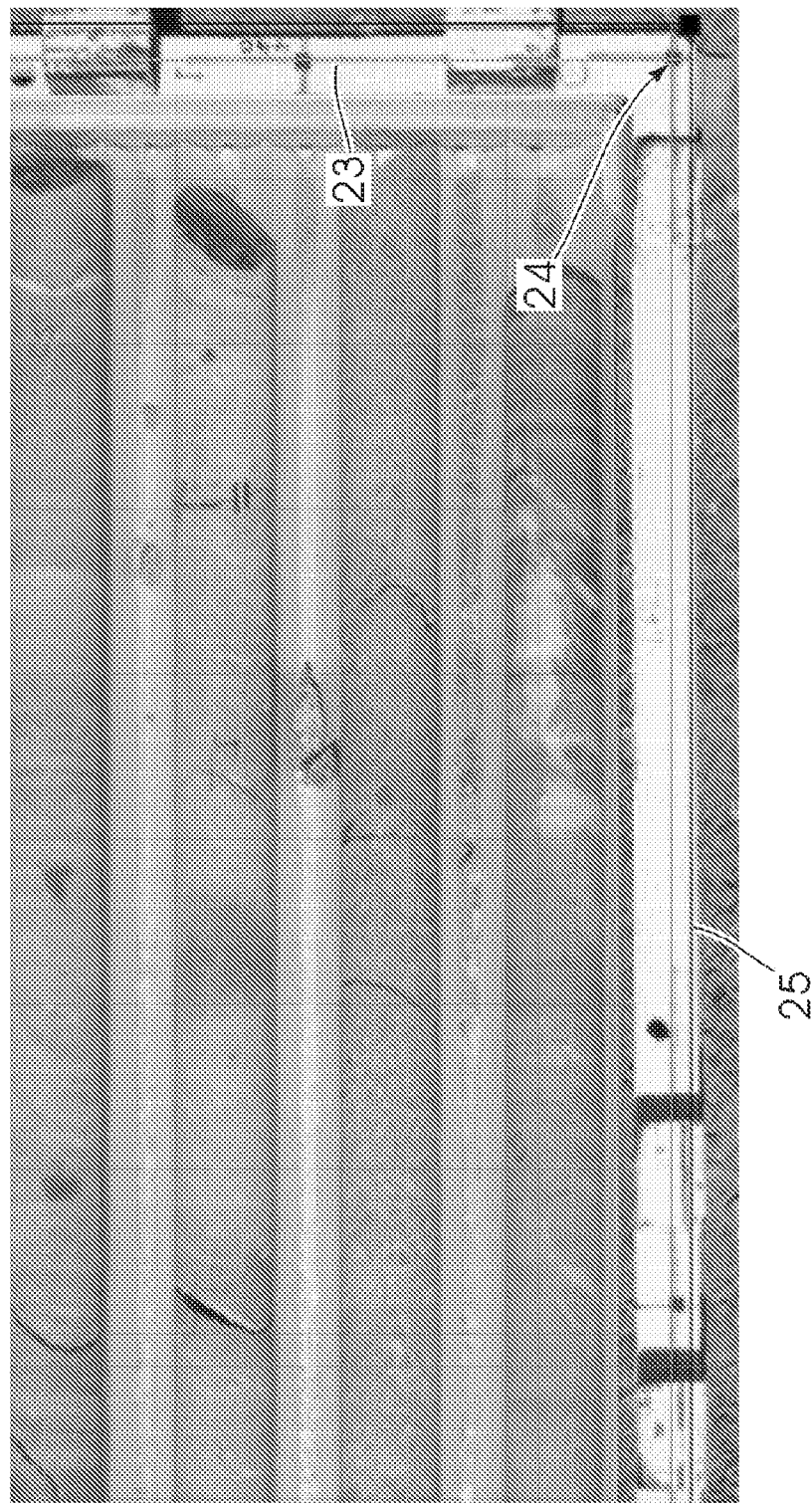

Once the image (1) has been corrected or un-distorted, the software generates green lines (23) across the image through red corner points (24) on the frame (11). It also generates blue lines (25) forming a rectangle across the image through the elevated blue lines (21) and crops the image (1) to what is seen in FIG. 8a. Where the lines (25) do not properly coincide with the lines (21) on the brackets (12), the sides (25) of the rectangle can be dragged into a correct overlying position. The lines (23) and (25) can be seen more clearly in Figure 8b. This is the product that is imported to the logging program on computer (F). The red points (24) mark the positions of selected using the red crosses (22) and remain on the image as an indication of accuracy.

It will be appreciated that alternative indicators on a frame (11) can be used for the calibration and correction. The frame (11) may also be made from any suitable materials. It need not be rectangular and a close fit to a core tray (6). The frame (11) may therefore vary in its configuration as long as it provides the necessary reference indicators or points required by the image processing software. Such a frame may also be made integral with a core tray or it may consist of more than one part for arrangement around a tray. The brackets (12) may also be inverted pieces of angle iron, with a blue line along the upward facing ridge, located centrally along the frame (11).

With the current image processing software, the photograph (1) can be taken with almost any digital camera from a reasonably central elevated position over the core tray (6). An image taken by hand standing over a core tray would be sufficient for processing.

Furthermore, where the qualities or characteristics that a particular camera and lens impart to a captured image (such as radial distortion, pitch and yaw perspective and depth perspective) are known, a scale is also not required to be included in the image. This is because the diameter of the core is known and provides a reference for measurement. Where the height of the camera fixed vertically above the core tray is known (i.e. distance from camera to core), the diameter of the can also be calculated.

After the photographs (1) have been processed they are imported into the core logging software program. The generated green (23) and blue (25) lines, in the corrected image (1), are detected and used to calculate the parameter required in order to compensate the measurement for depth perspective in the image (1).

The images (1) are now available for logging, which must preferably be done with the core (2) at hand for manual inspection. This is shown indicated by (G) in FIG. 3. The imported image (1) can be magnified on a computer screen if that is required.

Figure 9A:
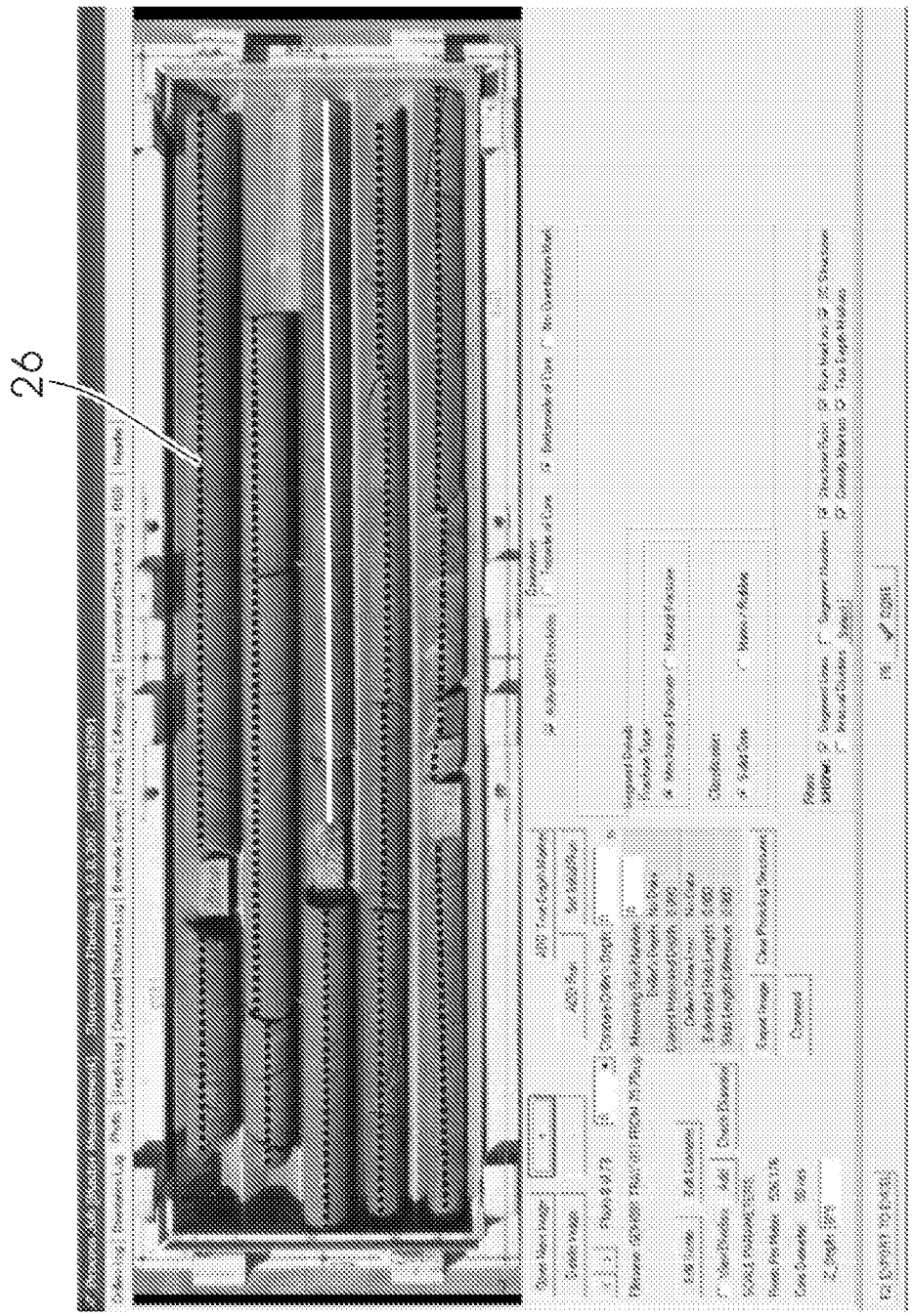
FIG. 9a shows a processed digital image of core samples imported to a software program.
Figure 9:
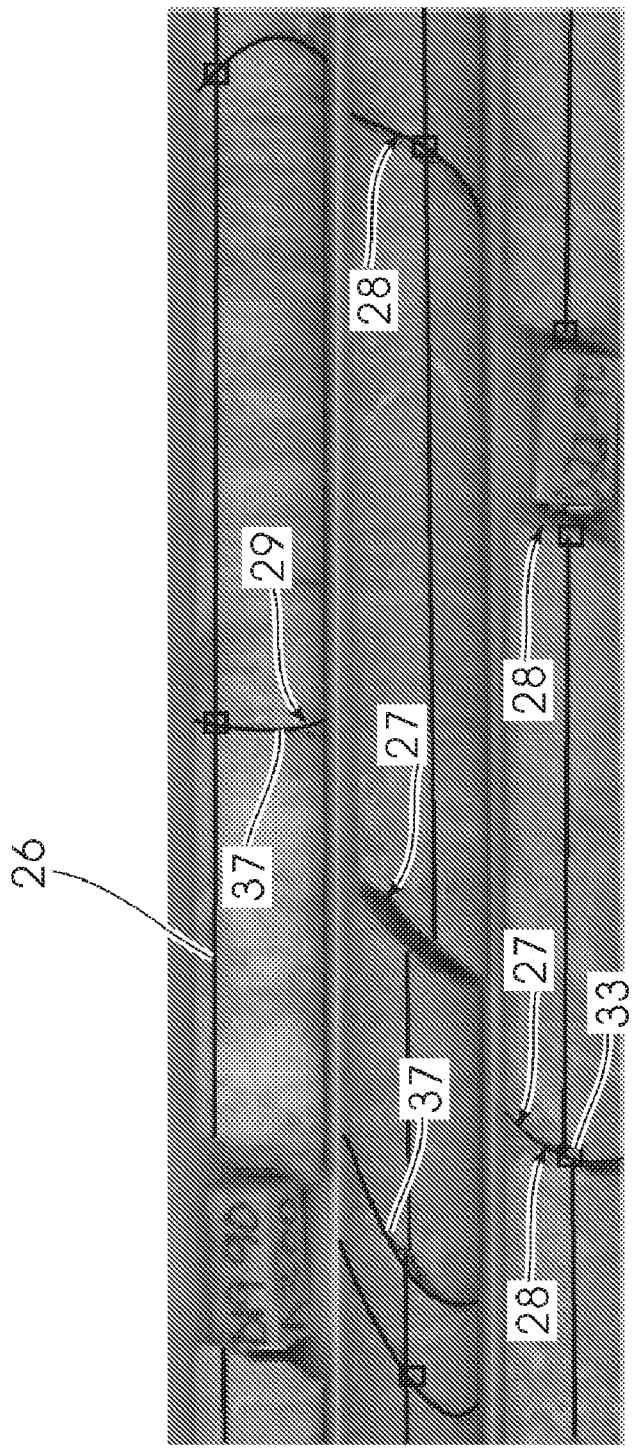
Figure 9:
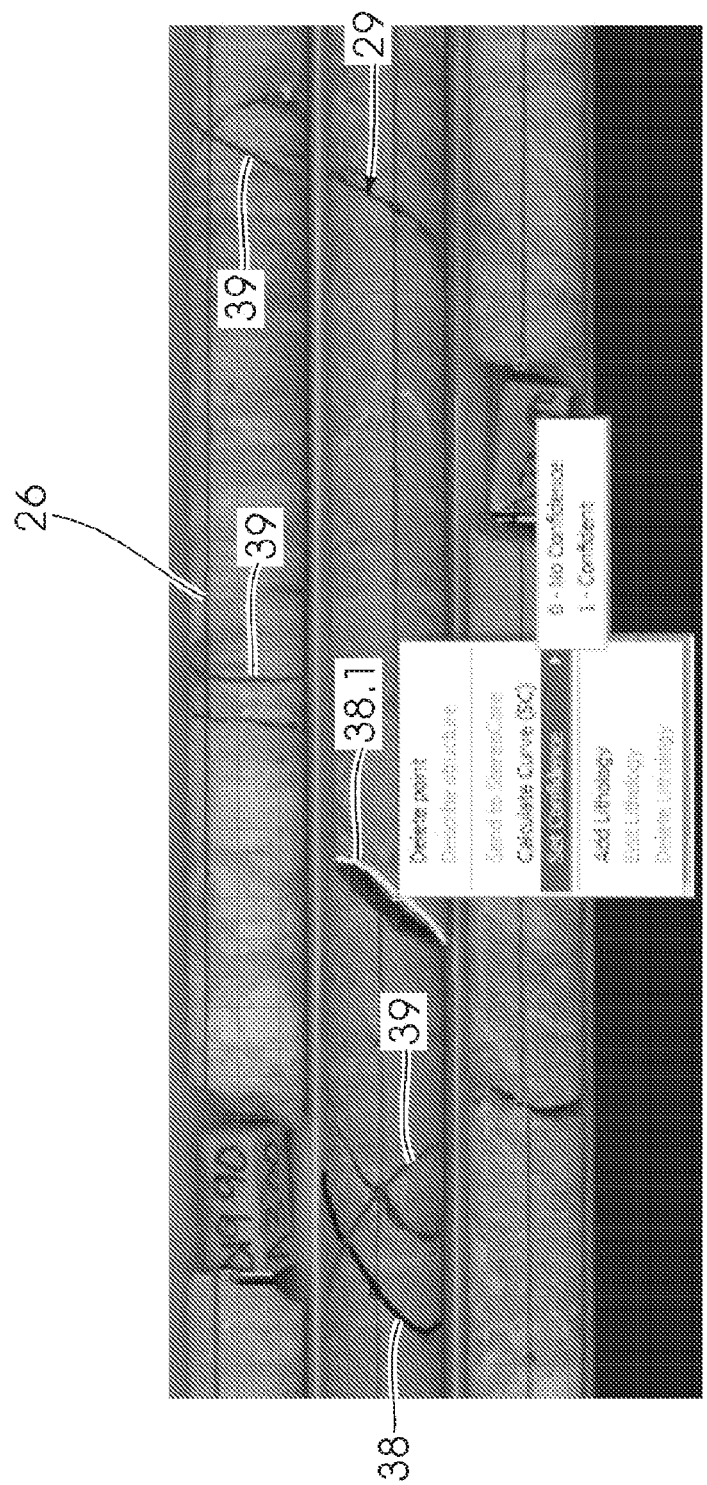

The first task is depth registration of the core (2)—see FIG. 9a. A depth—reference line (26) is generated along each segment of core (2) in the image (1). These lines (26) are to depth reference the core and create a "depth log".

Where the core (2) is oriented the reference line (26) is generated, using the logging program, directly over the orientation mark (7) on the photographed core (2). This is done by clicking the computer cursor first at the upper end and then at the lower end of the core segment (where the orientation mark meets the ends). The same marking (26) is made if the core (2) is not oriented. However, in this case, an estimation of where the core axis lies is used to generate the reference line (26).

A superimposed coloured reference line (26), in this example purple, will appear on the image (1) between the two points where the cursor was clicked. The logging program then prompts a selection from the following:

Bottom marked with orientation line—if selected, line (26) turns red;
Top marked with the orientation line—line (26) turns pink;
No orientation line—line (26) turns orange;
Matrix/rubble—line (26) turns yellow.

Orange lines on the image (1) therefore denote sections of un-oriented core, whereas a yellow line is used to demarcate zones of rubble or matrix. The selection of these colours is only by way of example. The benefit or convenience of such colour coding will however be appreciated.

The lengths of each individual solid and rubble section of core is recorded and numbered (not shown) on the image.

As mentioned, a marker or core block (10) reflecting a depth reading provided by the driller will be positioned at the start of each run of core (2) before the photograph (1) is taken. The depth of the bottom of the borehole is also known from the length of the drill string.

The start depth of every run of core will be entered into the program manually in accordance with the depth marker (10). In the image (1) the core (2) is depth referenced by clicking sequentially on the top (27) and bottom (28) ends of the reference line (7) on each run of core (2) or each individual segment of each run of core (2). The nearer the line (7) is to the crest of the core (2) the more accurate will be the depth registration of the core.

By incrementing the lengths of each segment in the run the total core recovered for the run is computed. Each run of core (2) may, as already mentioned, exist as more than one segment. Breaks in a core run (2) can result from the drilling or from naturally occurring cavities, joints or faults. Cavities will result in core loss but this can also happen where a driller has ground part of the core (2) away. The difference between consecutive depth markers (10) and the advance made in drilling the borehole will indicate where there has been core loss and the extent thereof. The software program provides fields for manual readings and notes based on a visual inspection. These readings are recorded to account for the irregularities. Occurrences of core gain may also present themselves and can be dealt with in the same manner. Gains in core result from the mechanism used to recover the core run from the bore or where the depth readings from the driller are incorrect.

This process of linear measurement and description enables automatic rock quality designation ("RQD"). A cumulative total is calculated and automatically compared with the "Driller's Log", which will have already been loaded onto the software program. This is to ensure accuracy in allocating and classifying any core loss at the end of every run. The length of the core stub left in-hole will also be computed, since the core block (10) depth records the depth of the cutting edge of the drill bit and not the exact core break in the run.

The logging will preferably take place at the drill site and with the core (2) shown in the image (1) being processed at hand. This is illustrated by (G) in FIG. 3 and by (D) in FIG. 1. The visual inspection referred to can thus be made with respect to the image (1) as well as the core sample (2) itself.

After depth registration the next task is measuring the geological structures found in the core, which fall into two categories: planar and linear structures. These are dealt with separately below. All structures are picked and breaks in the core are classified as natural or mechanical breaks. The marks made on the core in the preparation phase are used.

The term "picked" refers to selection of a structure followed by recording of its relative orientation using the logging program to enable calculation of $\alpha$, $\beta$ and $\theta$ angles (as appropriate) and a description of its characteristics. The term "pick" refers to such an entry.

The program is thus suited for recording a "Point Log" for each structure on a core segment. This includes both healed structures and open structures at the ends of a segment of core (2).

Figure 10:
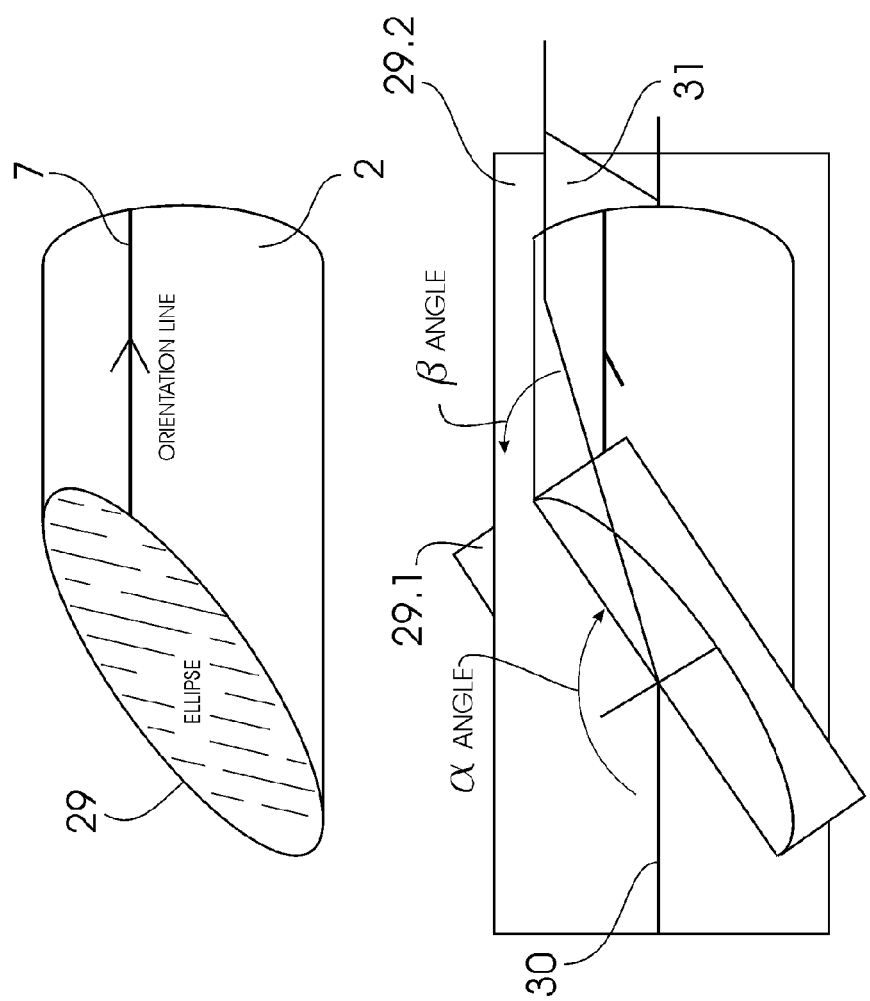
FIG. 10 shows an illustration of α and β angles.

All planar structures (29) have an elliptical outline in the core (2) as shown in FIG. 10. Such a structural plane (29) is thus also thus sometimes referred to as an ellipse (29) in this description. If the core (2) is oriented, measuring the attitude of the ellipse (29) relative to the core axis (30) and the known geographic vertical plane (31) enable these angles to be converted to the true in-situ dip and dip direction of the plane—given survey data for the borehole path. The attitude of the ellipse (29) relative to the core axis (30) is conventionally termed the alpha ($\alpha$) angle (i.e. the difference between the core axis and structural plane (29.1) of the ellipse). The attitude of the ellipse (29) relative to the known geographic vertical plane (31) is conventionally termed the beta ($\beta$) angle (i.e. the difference between the in situ vertical plane and the plane of the major axis (29.2) of the ellipse).

Figure 11:
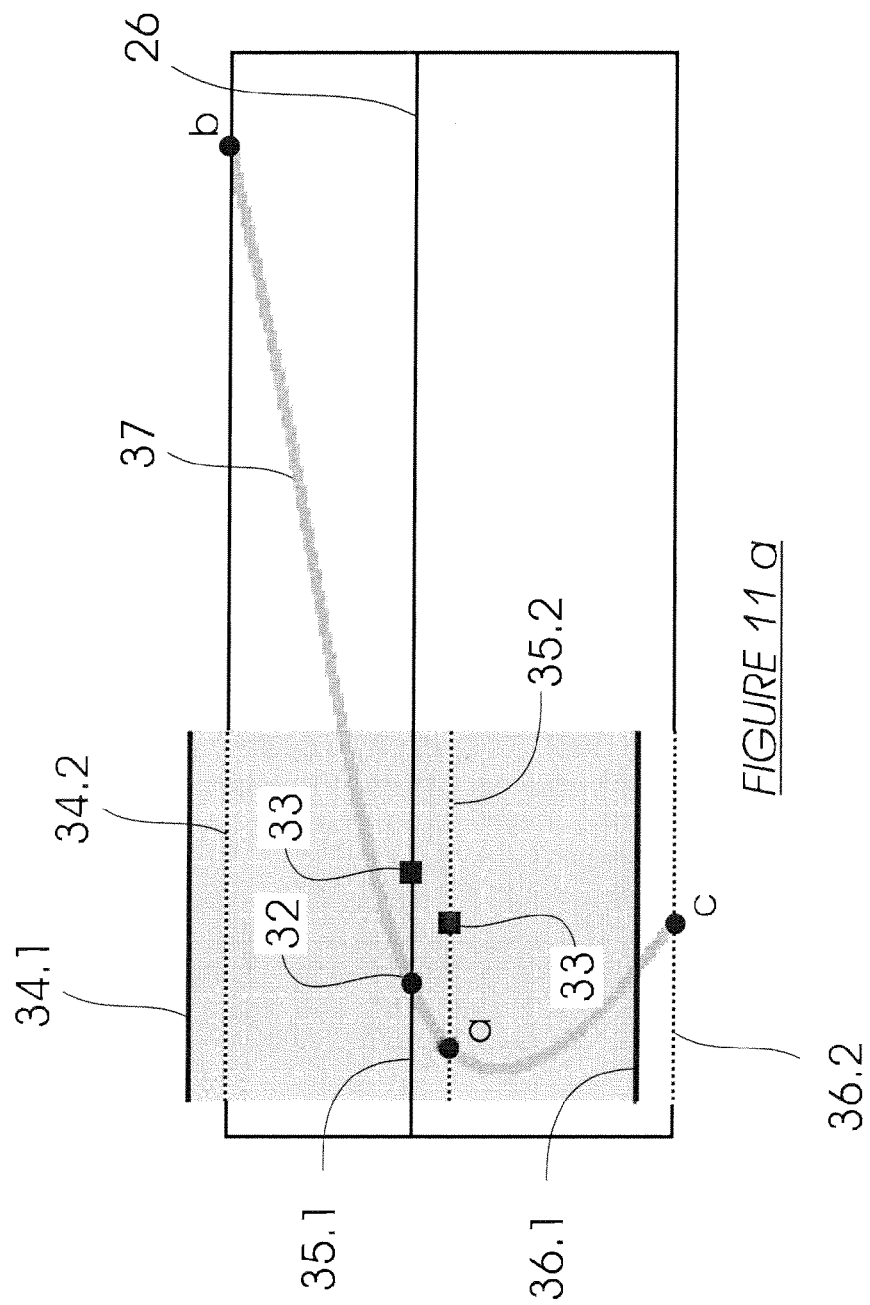
Figure 12:
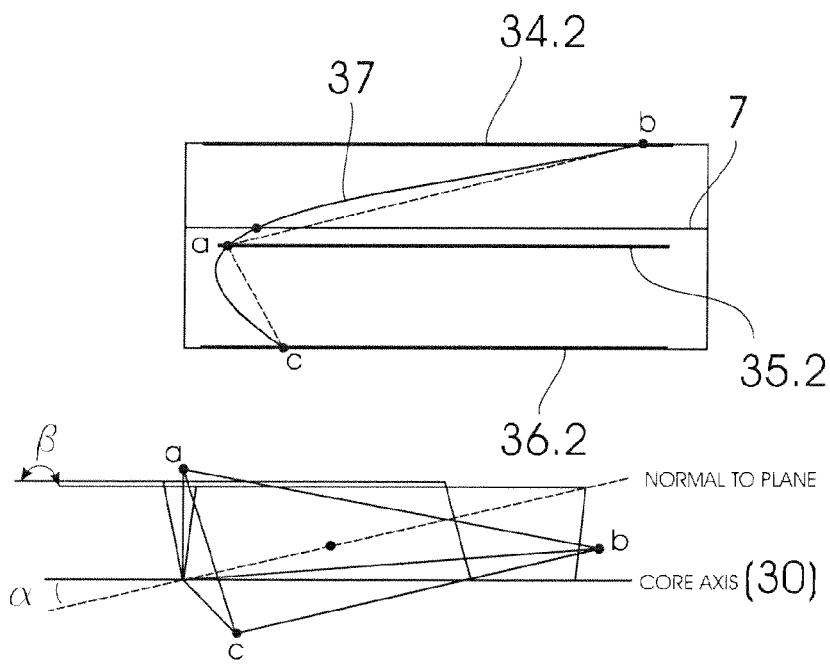
FIG. 12 shows a schematic illustration for the calculation of α and β angles for a planar feature.

With reference to FIGS. 11 and 12, the un-distorted and corrected image (1) provides a virtual three-dimensional representation of a cylinder of core (2). The diameter of the core (2) will be entered into the software program and corresponds to the width of the core (2) shown in the image (1). A sliding marker (33)—also referred to hereinafter as a "slide"—is moved along the reference line (26) generated by the program using the cursor. The cursor is clicked on the slide (33) when it is over the point where the structure that is to be picked intersects the reference line (26) and a marker (32) is placed at this point. Note the line (26) should be superimposed on the orientation line (7) of a marked core (2). On a second click of the cursor on the marked intersection point (32) of the (oriented) reference line (26) and the structural plane (29), the software will generate three lines (34), (35) and (36) parallel to the axis (30) of the core (2) over the image (1). The centre line (35) will be provided on the point (32) where the cursor was clicked.

These parallel lines are equally spaced apart from the reference line (26). More specifically, the side lines (34) and (36) will be spaced apart from the centre line (35) by a distance equal to the radius of the core (2). This is the first position of the lines (34.1), (35.1) and (36.1). The distance between the parallel lines is thus equal to the diameter of the core (2), to which the image (1) is calibrated. However, the core (2) is not always arranged in the tray (6) with its orientation line (7) at an apex position. For this reason, the parallel lines do not always match up at the sides of the core (2) in the image.

The three lines (34.1), (35.1) and (36.1) are then dragged, using the cursor, into a second position (34.2), (35.2) and (36.2). These lines can be dragged either up or down, again using the cursor, until they are aligned with the sides of the relevant core segment (2). In the second position, lines (34) and (36) are aligned with the sides of the core (2). The slide (33) on the centre line (35.2) is again located at the intersection with the structure and the cursor clicked. The angle represented by the adjustment of the centre line (35.2) will be factored in as a correction in the following calculations of the program. The movement required provides a measure of the offset of the oriented reference line (7) from the vertical plane as the core (2) lies in the core tray (4). This offset angle is then applied to the measurement and computation of the beta ($\beta$) angle of the structure. Without the capability of so defining this offset, the core would have to be placed in the tray with the reference line perfectly in the vertical plane (i.e. at the exact crest of the core cylinder) prior to the core being photographed.

Once lines (34) and (36) match the sides of the core segment, the cursor is clicked to fix them in position. Once the lines are set, and the cursor clicked, a second slide will appear on the top line. This is similarly located over the intersection of the side of the core with the structure and clicked. A third slide then appears on the bottom line. This is used to mark a third intersection and, once it is clicked, the program corrects the points for depth perspective and generates an ellipse in the form of a trace (37) through these three points or slides (b), (a) and (c), part of which is seen on the core (2) in the image (1). The cursor is in this way used to click on the points (b), (a) and (c) where the structural plane (29.1) intersects the three lines (34.2), (35.2) and (36.2). If the part-ellipse (37) coincides with the structure, the three points have been correctly located. The structure can be so recorded. The part-ellipses or traces (37) can be seen in FIGS. 9b.

Referring particularly to FIG. 12, between the point (a) on the centre line (35.2), which is a point of origin, and the two points (b) and (c) on the side lines (34.2) and (36.2) are two vectors which lie in the structural plane (29.1). The $\beta$ angle is thus computed by the software program. The two vectors are used to calculate a vector which is normal (the normal vector) to the structural plane. The normal vector is compared to the core axis (30) to provide the $\alpha$ angle of the structural plane (29.1). The exact shape of the ellipse (37) relative to the reference line (26) is thus detailed and the program automatically calculates the $\alpha$ and $\beta$ angles.

The logging software program automatically generates a coloured trace, in this example green, to overlie the structural planes [in other words, superimposed as the relevant part-ellipse (37)] as they are picked. This process therefore displays the green part-ellipses (37) on the image (1) which closely trace the outline of the structures on the core (2). These markings (37) remain visible on the image (1) or at least in one of the optional views that can be selected. It is from these ellipses (37) that the alpha and beta angles are automatically calculated and recorded in an "Orientated Structure Log".

Manual measurements of structures, where available and captured into program, are also displayed at their recorded depth locations on the image. In this embodiment, part-ellipses (38) that represent the manually plotted structures are coloured blue. A visual comparison with the structures on the image (1) gives a clear indication of the accuracy of the manual angle measurements. If the blue trace matches the structure on the image then the data set ($\alpha$ and $\beta$ angles) is allocated a confidence level of one. Where the traces do not match the structure the confidence level is then recorded as zero by right clicking on the trace and choosing the zero option displayed in a pop-up window. This action will also change the colour of the trace to red so that rejected data sets can be easily identified and corrected after the audit. Such a rejected trace is shown as (39). A trace that is being audited is indicated by (38.1) in FIG. 9c. The numeric data represented by these visual markings will also be compared in a table or in some other suitable manner. Therefore, in addition to the visual comparison on the image (1), a calculated difference in data sets will also provide a clear comparison of the manual measurements against the details logged in accordance with the aspects of this invention.

It will be understood that if the borehole path survey, giving detail of the in-situ changes in inclination and trend of the core axis with depth, is preloaded into the software program, the $\beta$ and $\alpha$ angle can automatically be rotated to their in situ dip and dip direction values. Fractures can also be marked over sections of un-oriented core, but for these picks only the alpha angle data is recorded in an "Un-oriented Structure Log".

Linear structures can be classed as either non-penetrative or penetrative. Non-penetrative refers to lineations that only occur on a structural plane such as slickensides and cleavage-bedding intersections, whereas penetrative lineations form part of the fabric of a rock such as a pervasive mineral alignment.

As already mentioned, the $\theta$ angle is required for lineations present on the core (2). In the case of non-penetrative lineations, such as striations formed on an open structure, a line (not shown) is generated along one of the striations that intersect the core axis up to the edge to the core. This is done using the cursor and once it is recorded, the program calculates the theta angle.

Figure 14:
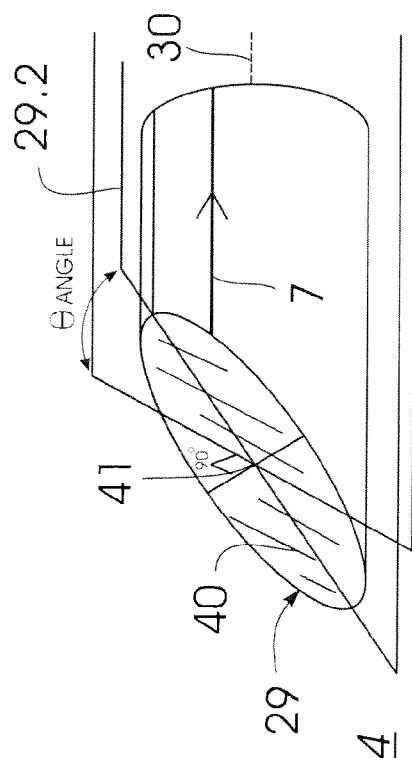
FIG. 14 shows a schematic representation for angular calculations relating to non-penetrative lineations.

The in situ plunge of any lineation lying in the plane of an open fracture is also referred to as the theta ($\theta$) angle. As non-penetrative lineations (40) lie in a plane (29) the attitude of the pole (41) to the structural plane (29) is automatically perpendicular to the lineation (40). Once the plane (29) has been measured, the $\theta$ angle between the lineation plane (42) and the ellipse major axis plane (29.2), uniquely defines the difference between the lineation trend and the known trend of the pole (41). This is illustrated in FIG. 14.

Figure 13:
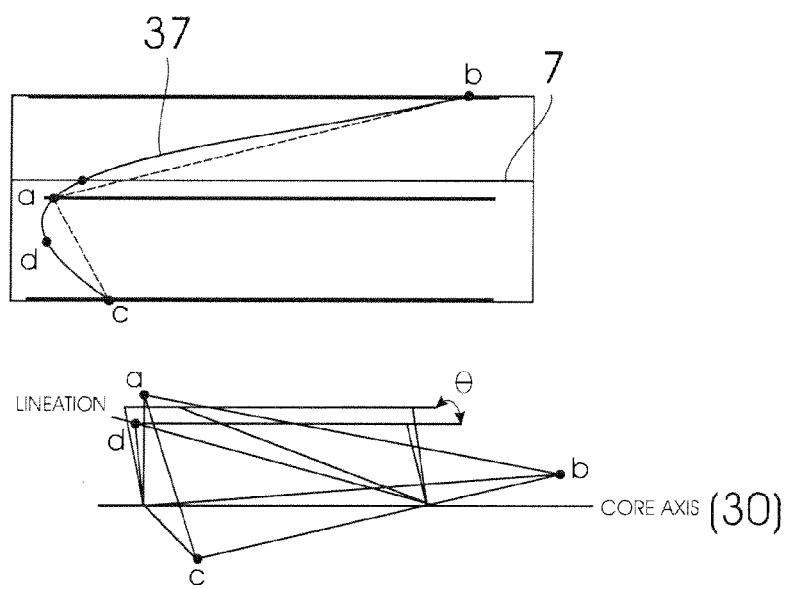
FIG. 13 shows a schematic representation for the calculation of α and θ angles for a lineation.

Referring to FIG. 13 as well, the $\theta$ angle will be recorded by manually inspecting the fracture face of the plane (29) to establish which lineation intersects the core axis (30) as well as the edge of the fracture (29). The point (d) where that lineation intersects the edge will be marked by clicking it on the image with the cursor. Having the core sample available enables a viable estimation, particularly when it is made by a suitably skilled person.

Figure 15:
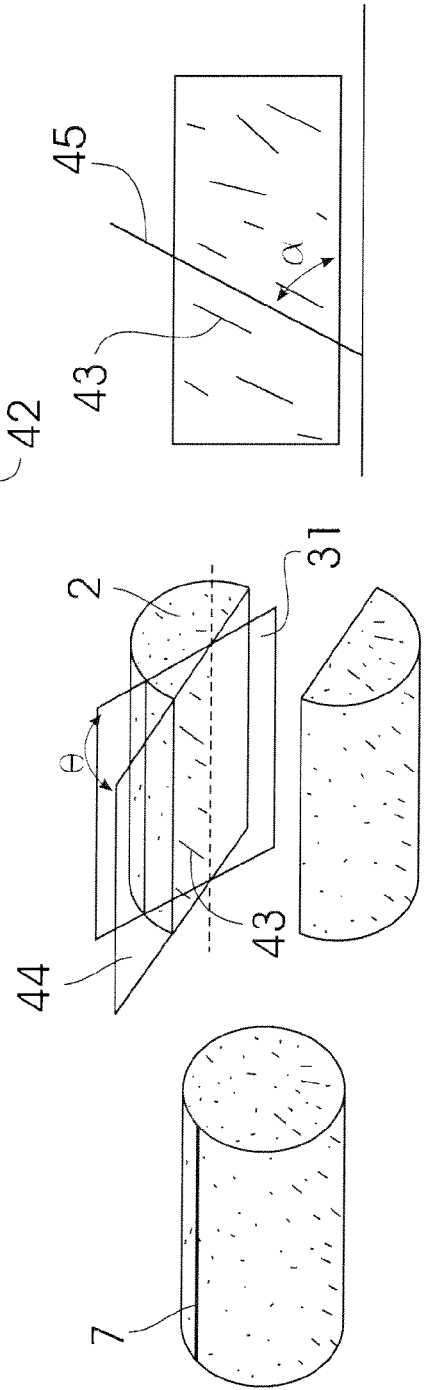
FIG. 15 show a schematic representation for angular calculations relating to penetrative lineations.

Referring now to FIG. 15, penetrative lineations (43) require both a theta ($\theta$) angle and an alpha ($\alpha$) angle to be measured relative to the geographic vertical plane (31) or, in other words, the reference line (7). For penetrative lineations, such as those formed by aligned needle-shaped minerals in the rock, the portion of the core with the most expression of the lineation and that with the least expression are identified.

First the lineation plane (44) is found. This is done by marking point on the image (1) where a lineation appears as a round dot on the surface of the core (2). The lineation plane (44) is defined as the plane bisecting the core (2) in which the linear feature (43) has its maximum extension. It is usual to mark the intersection of this plane with the core circumference down the length of the core sample (2) and then measure $\theta$.

This is followed by a determination of $\alpha$, being the pitch of the lineation (43) in the lineation plane (44). The core sample (2) must then be manually inspected to locate a lineation (43) that forms a line (45) along the surface of the core (2). A line parallel to the markings showing the most expression is generated and a dot marks a point at the position where the least expression is identified (not shown). The lineation line (45) is reproduced on the image using the cursor. This can be done by clicking on two points that would be located on the identified lineation line (45).

Once these marks are recorded, the software program calculates the $\theta$ and $\alpha$ angles from this information of the lineations.

In practice, an ellipse or trace (37) can be generated on the core image to calculate $\theta$ and $\alpha$ angles for penetrative lineations. The nose of the ellipse is placed at the point of least expression and the side of the ellipse overlies the area of most expression. This is simply done using the cursor.

Figure 16:
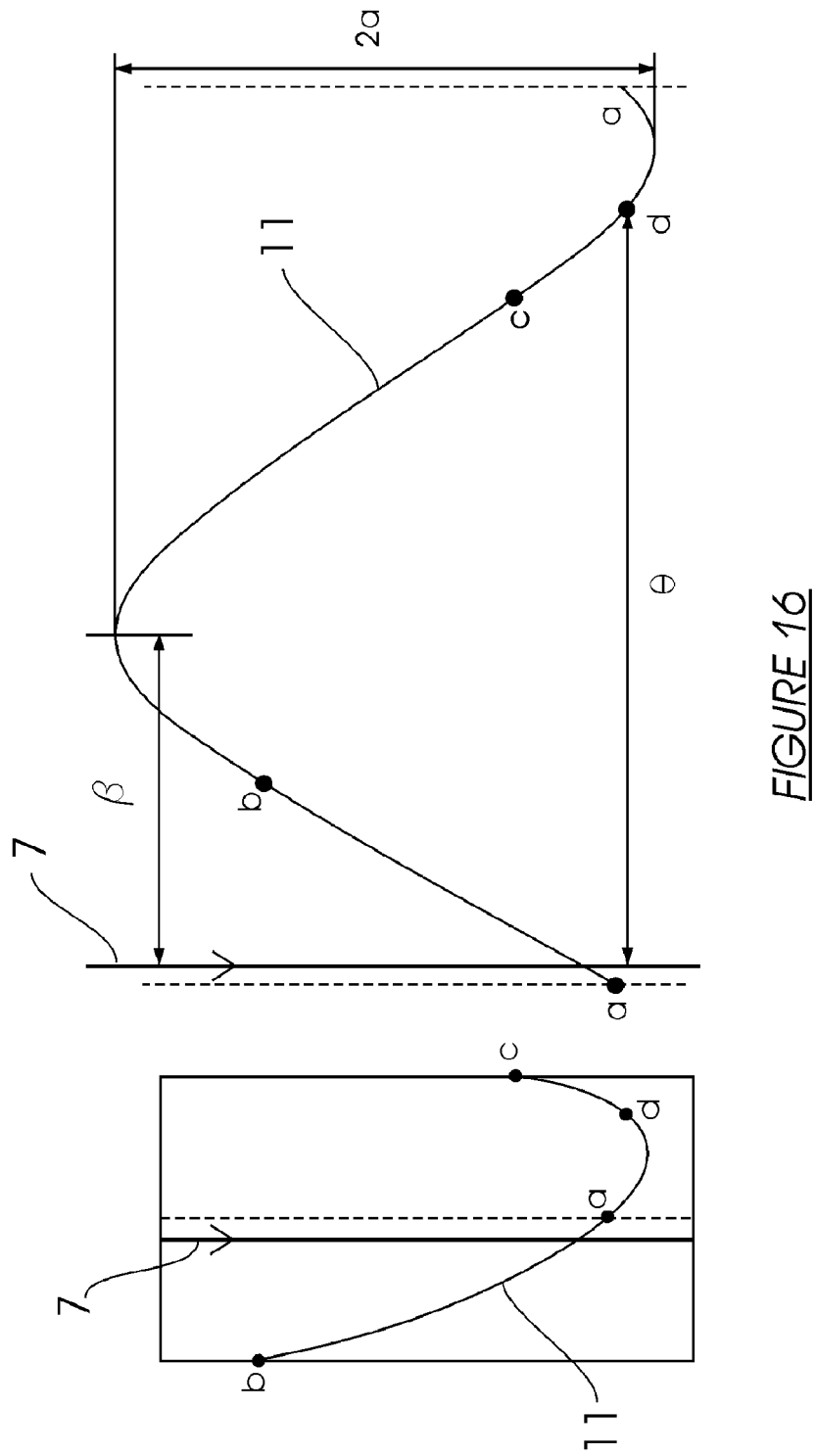
FIG. 16 shows schematic representations for an alternative calculation of α, β and θ angles.

Referring to FIG. 16, calculation of $\alpha$, $\beta$ and $\theta$ angles can also be made by the software program through unfolding the cylinder of the core (2) as shown. The elliptical structural plane (29) will be represented as a sine curve. This can be plotted by the software based on the structural features visible and recordable from the image (1). By marking three or more points on the ellipse (29) using the cursor, the graph can be plotted. In FIG. 16, the core (2) as it is seen in the image (1) is shown on the left with a graph indicating the angles on the right.

The software program will provide all the necessary fields for logging data, either manually or through computation. Prompts and menus made available as part of the program will facilitate the logging process.

Incremental processing of depth and then structure detail is carried out for each run up to the next core block (10). This emphasizes how much core (2) has been recovered, which is translated to a depth registration. In the process of core logging, the software thus enables recording of the measurement of depth along the core samples (2) from the borehole collar.

Also taken into account is that the "stick up" at the top of the drill string may vary for each of the runs. Normally, a constant stick up is subtracted from total length of drill string to get length of the rod string in the ground (i.e. borehole depth). However, each time the stick up is different it affects the run length. The driller provides a sheet with the "stick up" values for each run as well as recording the length of the inner tube of the core barrel. If more core is recorded as being recovered than the length of the inner tube, it indicates an error in measurement. If the driller's advance is longer than the inner tube length then core must either have been ground away or the borehole intersected a cavity resulting in core loss.

The usual incremental recording of data by a driller determines that any mistake is passed on throughout the results that follow. The logging software corrects these errors and ties up the runs that are being logged with the driller's runs (from the sheet).

The software thus provides for the necessary length (or depth) and angle measurements. Point logs including this data are recorded for each structure. The rest of the logging is done in "Interval Logs" where details of what can be seen on each section of core are set out. Clicking on a contact between two different lithologies intersected in the core, where the contact intersects the reference line, places a marker on the reference line in the image. Right clicking then displays a pop-up menu in which there is a choice to "Add Lithology". Clicking on this choice brings up an editable Lithological Dictionary where the rock type preceding the marker can be chosen and colour and text coded tags are then automatically placed on each segment of the interval so marked.

While what has been set out deals mainly with the measurement aspects of logging, the software will also specifically provide descriptive aspects of logging. These can be divided into core interval classification and structure classification. For the interval classification, we have already mentioned recording estimations of missing section but this also includes recording physical characteristics, such as whether the rock constitutes solid or rubble/matrix, as well as details of lithology, weathering and texture etc. The structure classification will include details of planar and linear features. The planar features could be open or healed fractures, bedding or cleavage amongst others. The linear features can be recorded as penetrative or non-penetrative, slickensides, mineral lineations etc.

The description of core (2) is normally quite subjective, depending on the preferences of a particular geologist. In this regard, the software will be flexible and easily customized to whatever the user prefers. The provision of graphic logs as part of the software for recording these descriptive details will be subject to customization depending on a particular person's logging preferences. That means that the presence and content of pop-up windows, drop down menus and other such features useful for description (see below) can be designed to the specific requirements of a user.

After the core losses or gains have been estimated for each run of core, the software program is enabled to automatically compute the true depths along the borehole path of all features logged in the core, eliminating the errors induced by core gain or loss that are normally not taken into account when logging the core manually. This is essential for meaningful comparison of the core logs with data derived from borehole geophysics where a variety of sondes are lowered into the borehole to measure various physical properties directly from the rock at depth. Once the core has been depth registered and a survey of the borehole path has been loaded, the program is further enabled to compute the true vertical depth and geographic coordinates of every feature logged.

Co-ordinates for down-hole features are calculated and plotted in a desired format. While the data will generally be presented in table form as it is logged, in the case oriented core, it is also simultaneously plotted on a Stereonet display. This representation of three-dimensional data is well known to those skilled in the art and will not be described in any detail. The software will furthermore provide for automated three-dimensional ground modeling based on the data that is logged from oriented core.

Figure 18:
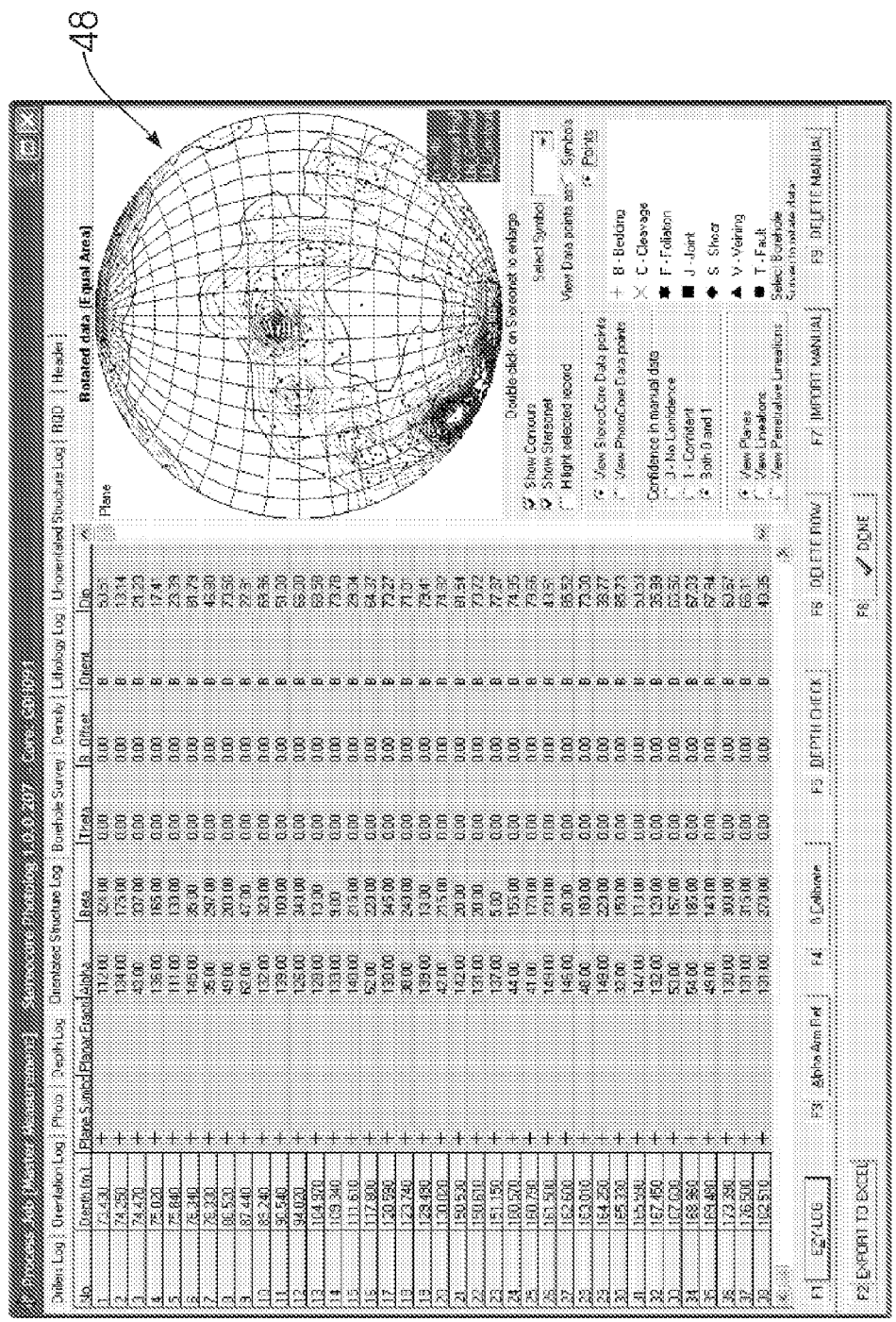
FIG. 18 shows some of the details logged on the software program and plotted on a Stereonet.

Once the borehole survey information is loaded into the program all alpha and beta angles are rotated, according to the trend and plunge of the core axis at the depth from which each structure was measured, to derive true dip and dip direction. The poles to these planes are then displayed and contoured on an Equal Area Stereonet plot (48), which can be seen in FIG. 18.

The three-dimensional ground modeling will normally follow confirmation and refining of the "measured whilst drilling borehole survey" results with data from an "independent borehole survey". Once the data from non-oriented core is verified in this manner, there will be limited ground interpretation and correlation provided which is also of value.

The software provides fields for equivalent "measured whilst drilling borehole survey" results and "independent borehole survey" results to be independently loaded and interchangeably used for calculation and display. The structural measurements will include "raw" data displayed simultaneously on an Equal Angle Stereonet, as mentioned, and "rotated" data displayed simultaneously on an Equal Area Stereonet. The raw data is measured relative to the core axis only while the rotated data are in situ values relative to the borehole itself.

The software enables dry density values to be computed for segments of core (2) that have a clean planar feature picked at either end. The volume of the stick or segment can be determined and all that is required for the density calculation is to enter an accurate weight of that portion of the core sample. The software program will also be enabled for automatic calculation of, amongst others, Rock Quality Designation (RQD) and Rock Mass Index (RMI). Information will be displayed as geotechnical logs and "tadpole" plots for both plane and lineation data.

As already suggested, the method and software enable the recording of details regarding the rock core quality. A "core quality index" derived from the core loss and recovery parameters will be presented with the other data.

Figure 17:
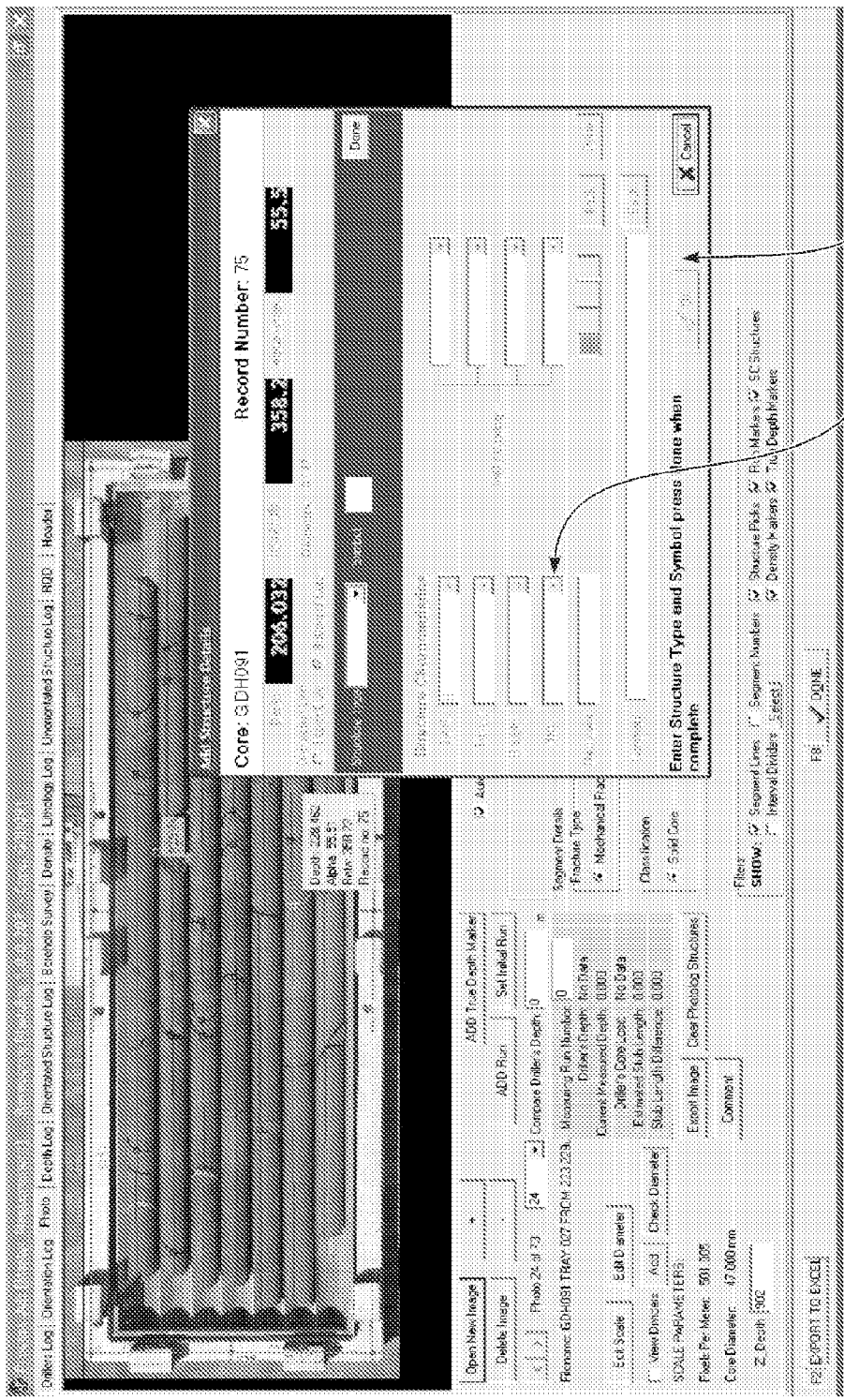
FIG. 17 shows a window for entering details into the software program.

It will be appreciated that the system removes much of the uncertainty from geotechnical core logging. All depth and angular measurement is done through precise image processing that delivers a fully auditable and permanent record. Such reliably marked up images (1) allow the geologist to fully concentrate on examining the core (2) and make detailed and accurate description of all the structures identified. Referring to FIG. 17, the logging software program provides a pop-up window form (46) for such description. This window is activated by right clicking on the selected structure. The form has several drop-down menus (47) providing a variety of choices from classifying the structure (as bedding, cleavage, joint, foliation etc.), to describing it in detail (as rough or smooth, planar or curved etc.). Provision is also made for recording the mineralogy of any infill as well as comment on any out of the ordinary observations.

In the case of non-oriented core, joint separation for planar features and attitude to core axis for linear features will be recorded. Where the core has been oriented, the dip and dip direction of planar features and the plunge and plunge direction of linear features are recorded. All the structural data is therefore recorded in either the Oriented or Un-oriented structural log, depending on whether the core segments (2) have an oriented reference line (26) or not. Both of these logs, together with the driller's log, depth and density logs can be exported to a Microsoft Excel program (or equivalent) for importing into other programs for further analysis.

However, given the borehole survey data the software program automatically rotates the oriented data to display the results as a contoured stereogram (48). Small circles can then be drawn on the Stereonet (48) to select clusters of data which allows for in-depth analysis of the various physical features that make up the cluster. Data for plotting on the Stereonet (48) can also be selected by depth or by structure type or both and synoptic reports generated. These reports will include: Depth registration logs detailing core loss/gain per run and true depth; True vertical depth (TVD) logs of all structural readings and lithological contact intersections; Workbooks for each borehole detailing the following on separate spreadsheets: (i) Raw manually logged structural data provided. (ii) Data filtered and discarded for analysis—with reasons. (iii) Confirmed data. (iv) Rejected data—with reasons. (v) Digitally re-measured data for rejected structures (vi) Logged fracture frequency along the core (vii) Percent confidence in the raw data provided and in the final re-processed data. (viii) Stereoplots for total core, by selected depth intervals and by lithologies intersected in the borehole.

The software programs described comprise (i) image processing and (ii) core logging applications. The image processing software can be provided as a separate package which is retained by the proprietor or service provider. The logging package, including the various aids for core preparation, is then made available to users under contract.

The image processing can be carried out by the proprietor and charged on a per meter basis. This work will normally be done off-site, using, for example, secure email to transmit the images with a rapid turn-around time limit. On-site training for operating the logging package will be charged on a daily basis.

What is set out with regard to the software described above, explains to some extent the requirements for operation and for the calculations. In another version of the image processing software, the elevated blue (20) and green (19) lines on the frame are detected by the program. The image (1) is processed and corrected as mentioned above automatically. A suitably taken photograph (1) of a core tray (6) in an appropriately marked frame (11) is all that is required.

Furthermore, in this version, the orientation lines (7) will be drawn onto the core samples (2) with a marker that is recognized by what may either be the image processing or logging software. Automatic depth readings are in turn generated for the portions of solid core (2). The core blocks (10) will also be recognized and cross referenced with the depth readings provided with the driller's log. In addition to this, a core tray with ridges visible between the core samples (2) will be used. The ridges will also be recognized by the software to provide a true diameter reading and to also generate a central reference line (26). The angular difference between this line (26) and the recognized orientation line (7) will be calculated automatically for corrections when providing alpha and beta angle measurements for structures.

It follows that planar structures, both open and healed, can also either be manually traced with a suitable marker that is detected by the software for automatic alpha and beta angle calculations, or the software can be adapted and trained to recognize such structures without necessarily marking them. The same applies to markings that will enable theta angle calculations for lineations.

While these and other readings or data recordings may be automated, the option of making corrections is always available. Information that requires judgment and estimation will be introduced in the ordinary interactive manner by a suitably skilled person. Importantly, the image (1) of the core is always available and inaccurate automatic tracers or markers generated as described can be scrutinized and corrected.

It will be appreciated that the inclusion of a measurement scale (C) in the image is not essential. A particular magnification and fixed distance between the camera and core will allow calibration—the average core diameter is normally known.

The photograph also provides historical detail of the core as it was when it came out of the core barrel. Any subsequent damage can therefore be attributed to mechanical breakage that may have happened in transportation to the core shed or storage.

For optimum results best practice calls for a comprehensive logging technique that keeps pace with the drilling rate and immediately presents the results for analysis and evaluation. The invention provides a means of achieving this and presents a saving in the time taken for proper core logging. It further provides an accurate visual record of the core, which can be revisited at a later stage for comparison to the logged data or for any other reason. The importation of manually recorded data which can then be fully audited for validity is another advantageous feature.

The software will be provided on a suitable computer readable medium and can be used with any combination of hardware suited for the purpose set out above. In so far as hardware is concerned, it is mainly a digital camera connectable to a computer that is required. These components could however be integrated into a dedicated machine.

A suitably skilled person will appreciate that a number of variations may be made to the described embodiments or aspects described without departing from the scope of the current invention. In particular, the collection of the data and computation of angles from the calibrated image are not limited to what has been set out in this description.

The invention claimed is:

1. A method of logging rock core, which includes taking a digital photograph of core from a borehole to provide a two-dimensional image of the core and operating a computer to:
   analyze the two-dimensional image and provide a virtual three-dimensional model of the core from the photograph; and
   record measurements of features of the core from the model.

2. A method as claimed in claim 1 in which the photograph is taken of a series of rock core runs arranged in a core tray with a longitudinal reference line drawn along the core.

3. A method as claimed in claim 1 in which the measurements include linear rock interval measurements and/or angular measurements of geological structures.

4. A method as claimed in claim 3 in which the linear rock interval measurements include the length of a segment of core and/or the position of a geological structure along the length of a segment of core.

5. A method as claimed in claim 3 in which the angular measurements include the angle, β angle and/or θ angle of a geological structure.

6. A method as claimed in claim 1 which includes calibrating the photograph to a measurement scale photographed with the core.

7. A method as claimed in claim 1 in which a correction scale is included in the photograph and which includes making corrections for depth perspective.

8. A method as claimed in claim 1 in which a correction scale is included in the photograph and which includes making corrections for radial distortion, pitch distortion and/or yaw distortion.

9. A method as claimed in claim 1 in which a reference frame providing a measurement scale and a correction scale is located around a core tray and is used to calibrate the photograph to the measurement scale and to correct the photograph for depth perspective, radial distortion, pitch distortion and/or yaw distortion to the correction scale.

10. A method as claimed in claim 9 in which the reference frame has indicators with known dimensions providing the calibration scale and/or the correction scale.

11. A method as claimed in claim 10 in which the frame is rectangular with indicators on an upper surface marking intersections of length and breadth adjacent to corners of the frame and in which the mid-points of the length and breadth are marked with indicators.

12. A method as claimed in claim 11 in which orthogonal lines provide indicators on the upper surface and the indicators include lines extending across elevated portions vertically above the orthogonal lines and parallel to the upper surface of the frame.

13. A method of logging rock core comprising, taking a digital photograph of core from a borehole, importing the photograph into a computer for:
    image processing wherein the image of the photograph is calibrated to a measurement scale and corrected for depth perspective; and
    data logging wherein measurements of features of the core are recorded from the processed image.

14. A method as claimed in claim 13 in which the image processing includes correction of the image for radial distortion, pitch distortion and/or yaw distortion.

15. A method as claimed in claim 13 in which the photograph is marked by the computer for corrections relating to at least depth perspective.

16. A method as claimed in claim 13 in which a reference frame and/or the core are marked with indicators and the computer is enabled to recognize the indicators and to automatically calibrate and correct the image.

17. A method as claimed in claim 15 in which the computer automatically measures the length of each segment of core in the image.

18. A method of logging rock core comprising operating a computer enabled by an image processing software program to receive a digital image of a series of rock core runs from a borehole and to: calibrate the image to a measurement scale; and correct the image for depth perspective.

19. A method as claimed in claim 18 in which the computer is operated to correct the image for radial distortion, pitch distortion and/or yaw distortion.

20. A method as claimed in claim 18 in which the computer is enabled to store data relating to indicators on a reference frame included in the digital image and to automatically calibrate and correct the image from the stored data.

21. A method as claimed in claim 18 in which the computer is enabled by a logging software program to make linear and/or angular measurements of features of the core from the image.

22. A method as claimed in claim 21 in which the computer is enabled to recognize markings in the processed image and to automatically calculate at least some of the measurements.

23. A computer enabled by a software program and operated to receive a digital image of rock core from a borehole, to calibrate the image to a measurement scale and to make linear rock interval measurements and angular measurements of geological structures of the core from the image.

24. A computer as claimed in claim 23 which is enabled to register indicators on a correction scale and to correct the image for depth perspective, radial distortion, pitch distortion and/or yaw distortion.

25. A computer as claimed in claim 23 which is enabled to automatically calibrate the image to a measurement scale and/or correct the image to a correction scale for depth perspective, radial distortion, pitch distortion and/or yaw distortion.

26. A computer as claimed in claim 25 which calculates the length of each segment of core and/or the depth of each geological structure in the image.

27. A computer as claimed in claim 25 which enables the angular and/or linear measurement results to be permanently stored on the image.

28. A computer as claimed in claim 23 which is enabled to import manually logged angular and/or linear interval data for comparison with structure seen in the image.

\* \* \* \* \*